(12) United States Patent
Wei et al.

(10) Patent No.: US 11,840,526 B2
(45) Date of Patent: Dec. 12, 2023

(54) COMPOUNDS AND METHOD FOR PREPARING THE SAME

(71) Applicants: BEIJING GRAND JOHAMU PHARMACEUTICAL COMPANY, LTD., Beijing (CN); NANJING GRITPHARMACO., LTD., NanJing (CN)

(72) Inventors: Weiye Wei, Beijing (CN); Jiannan Yang, Beijing (CN); Xiaotao Wu, Beijing (CN); Taotao Zhao, Beijing (CN); Hao Wang, Beijing (CN); Chao Li, Beijing (CN); Lei Qu, Beijing (CN); Bin Wang, Beijing (CN)

(73) Assignees: BEIJING GRAND JOHAMU PHARMACEUTICAL COMPANY, LTD., Beijing (CN); NANJING GRITPHARMACO., LTD., Nanjing (CN)

( * ) Notice: Subject to any disclaimer, the term of this patent is extended or adjusted under 35 U.S.C. 154(b) by 0 days.

(21) Appl. No.: 17/900,071

(22) Filed: Aug. 31, 2022

(65) Prior Publication Data

US 2023/0365535 A1    Nov. 16, 2023

(30) Foreign Application Priority Data

May 10, 2022   (CN) .......................... 202210500289.8
May 10, 2022   (CN) .......................... 202210500291.5

(51) Int. Cl.
*A61K 31/427*   (2006.01)
*C07D 403/14*   (2006.01)
*A61P 31/14*    (2006.01)

(52) U.S. Cl.
CPC .......... *C07D 403/14* (2013.01); *A61K 31/427* (2013.01); *A61P 31/14* (2018.01)

(58) Field of Classification Search
CPC .................................................. A61K 31/427
See application file for complete search history.

(56) References Cited

FOREIGN PATENT DOCUMENTS

WO    2022035911 A2    2/2022

OTHER PUBLICATIONS

Unoh, Yuto, "Discovery of S-217622, a Noncovalent Oral SARS-CoV-2 3CL Protease Inhibitor Clinical Candidate for Treating COVID-19", Journal of Medicinal Chemistry (2022), vol. 65, pp. 6499-6512.
CN First OA and First Search dated Jun. 14, 2022 issued in CN202210500291.5.
CN First OA dated Jun. 15, 2022 issued in CN202210500289.8.
CN Second OA dated Jul. 6, 2022 issued in CN202210500289.8.
CN Second OA dated Jul. 6, 2022 issued in CN202210500291.5.

*Primary Examiner* — Brian E McDowell
(74) *Attorney, Agent, or Firm* — Scully, Scott, Murphy & Presser, P.C.

(57) ABSTRACT

The present invention provides a composition comprising a compound of formula (I) or a physiologically acceptable salt thereof, in which the compound of formula (I) or a physiologically acceptable salt thereof has a HPLC purity of ≥90%;

formula (I)

wherein $R_1$, $R_2$, X and n are as defined herein. The present invention further provides use of the composition according to the present invention for preparing and/or purifying a composition comprising a salt of the compound of formula (I), and a method for treating a disease caused by a coronavirus which comprises administering the composition of the present invention to a subject. The composition of the present invention comprises the compound of formula (I) with high purity, and has good fluidity and anti-caking property; moreover, the claimed composition comprising the compound of formula (I)) with high purity is more suitable for preparing a composition comprising a salt of the compound of formula (I) with higher purity.

19 Claims, 10 Drawing Sheets

COMPOUNDS AND METHOD FOR PREPARING THE SAME

TECHNICAL FIELD

The present invention relates to a method for preparing a compound, and in particular to a method for preparing a compound with high purity.

BACKGROUND

Coronavirus belongs to Coronavirus genus, and is a positive-stranded RNA virus having an envelope. Coronavirus is becoming a research hotspot in the field of virology due to the outbreaks of Severe Acute Respiratory Syndrome (SARS) in 2003 and Middle East Respiratory Syndrome (MERS) in 2012. Novel coronavirus pneumonia (Corona Virus Disease 2019) is a new acute respiratory infectious disease caused by SARS-CoV-2 (also called 2019-nCoV). Since its outbreak at the end of December 2019, it has left more than 200 million people infected and over 4 million people dead around the world. It has become a global major public health event at present, and has greatly affected global social economy.

2019 novel coronavirus (2019-nCoV) is a novel strain of coronavirus that has not previously been found in humans. At present, for novel coronavirus infection(s), clinically supportive treatment is mainly performed, and no specific antiviral drug is available. In view of the severe situation of epidemic situation, there is an urgent need for practical and effective treatment means.

The prior art (Yuto Unoh et al., "Discovery of S-217622, a Noncovalent Oral SARS-CoV-2 3CL Protease Inhibitor Clinical Candidate for Treating COVID-19", *J. Med. Chem.*, 2022) discloses that a candidate compound S-217622 (i.e., (6E)-6-[(6-chloro-2-methyl-2H-indazol-5-yl)imino]-3-[(1-methyl-1H-1,2,4-triazol-3-yl)methyl]-1-(2,4,5-trifluorobenzyl)-1,3,5-triazinane-2,4-dione, hereinafter sometimes referred to as compound 1) may be used to treat COVID-19. Nevertheless, this document describes that the yield of step d (i.e., the step of reacting a solution of 6-ethylthio-3-[(1-methyl-1H-1,2,4-triazol-3-yl)methyl]-1-(2,4,5-trifluorobenzyl)-1,3,5-triazine-2,4(1H,3H)-dione and 6-chloro-2-methyl-2H-indazol-5-amine in THF in the presence of LHMDS) in the method for preparing the compound S-217622 is low (25%), and thus it is not suitable for industrial mass production.

SUMMARY

In addition to the above problems of the prior art, the inventors of the present invention found that the target product of step d disclosed in the above document has a purity of about 86% and cannot meet pharmaceutical requirements after repeated experiments on the method of the above document. Particularly, the inventors of the present invention found that impurities are easily generated in the step d of this document, and that these impurities are similar in structure and polarity to S-217622 and are difficult to be purified by conventional methods. Moreover, the impurities contained in the final drug product may reduce the efficacy of the drug and affect the stability of the drug, and some impurities are harmful to the human health or generate other toxic and side effects.

Therefore, there is a need to provide a composition comprising a compound of formula (I) with high purity to meet increasingly urgent requirements of industrial production and formulation development.

In a first aspect of the present invention, it provides a composition comprising a compound of formula (I) or a physiologically acceptable salt, in which the compound of formula (I) or a physiologically acceptable salt has a HPLC purity of ≥90%;

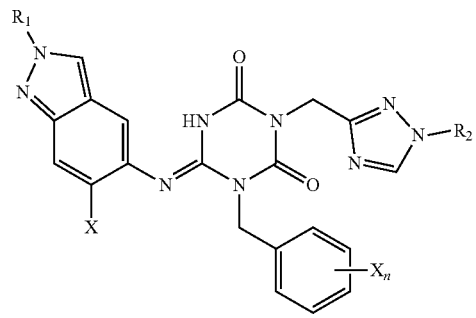

formula (I)

wherein $R_1$ and $R_2$ are each independently $C_1$-$C_6$ alkyl;

X is halogen; and n is an integer from 1 to 5.

In a second aspect of the present invention, it provides use of the composition according to the present invention for preparing a composition comprising a salt of the compound of formula (I).

In a third aspect of the present invention, it provides a method for treating a disease caused by a coronavirus, in which the method comprises administering a therapeutically effective amount of the composition according to the present invention to a subject.

Compared with the prior art, the composition according to the present invention comprises the compound of formula (I) or a physiologically acceptable salt with high purity, good fluidity and/or anti-caking property. Moreover, the composition comprising the compound of formula (I) with high purity is more suitable for preparing a composition comprising a salt (e.g., fumarate salt thereof) of the compound of formula (I) with higher purity (e.g., greater than 99% (HPLC) purity), meeting pharmaceutical standards while facilitating formulation development requirement.

DETAILED DESCRIPTION

Figure 1:
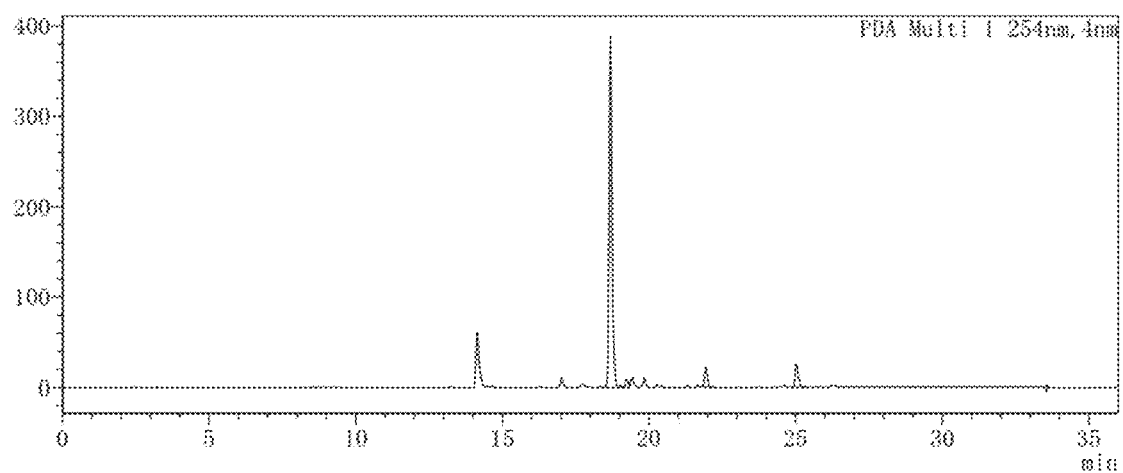
FIG. 1 is a HPLC chromatogram of the compound prepared in Comparative Example 1.
Figure 2:
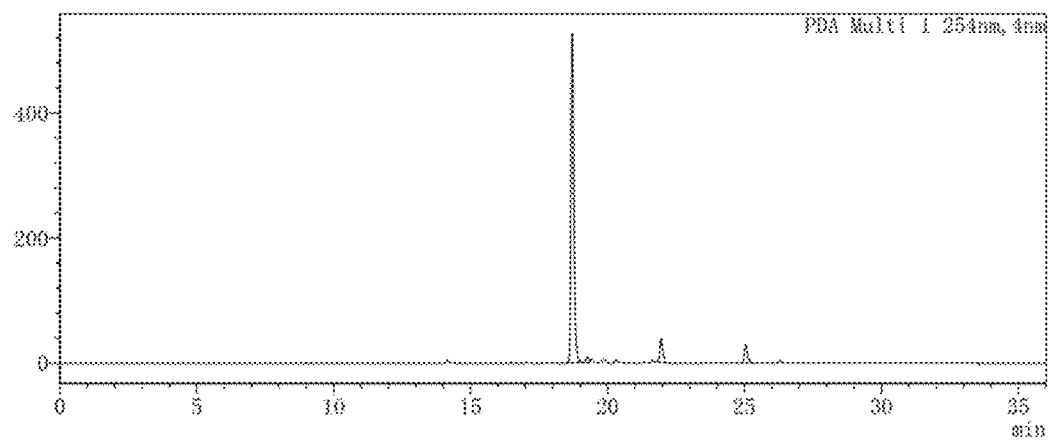
FIG. 2 is a HPLC chromatogram of the compound prepared in Comparative Example 2.
Figure 3:
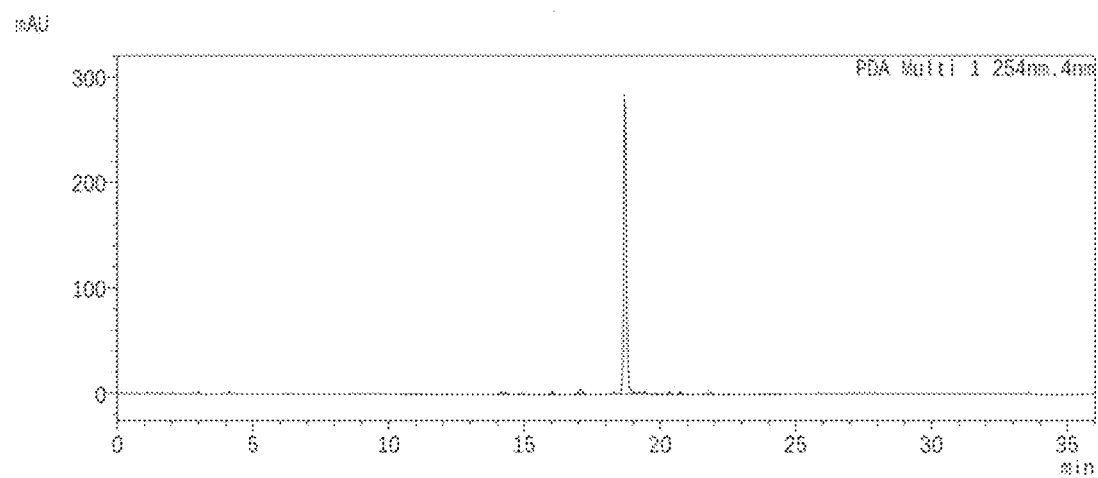
FIG. 3 is a HPLC chromatogram of the compound prepared in Example 3.
Figure 4:
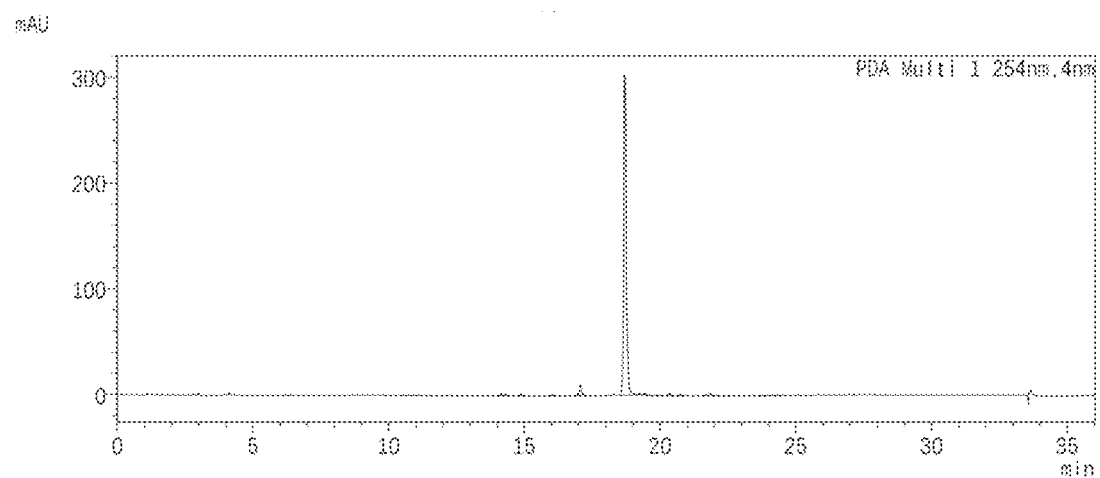
FIG. 4 is a HPLC chromatogram of the compound prepared in Example 8.
Figure 5:
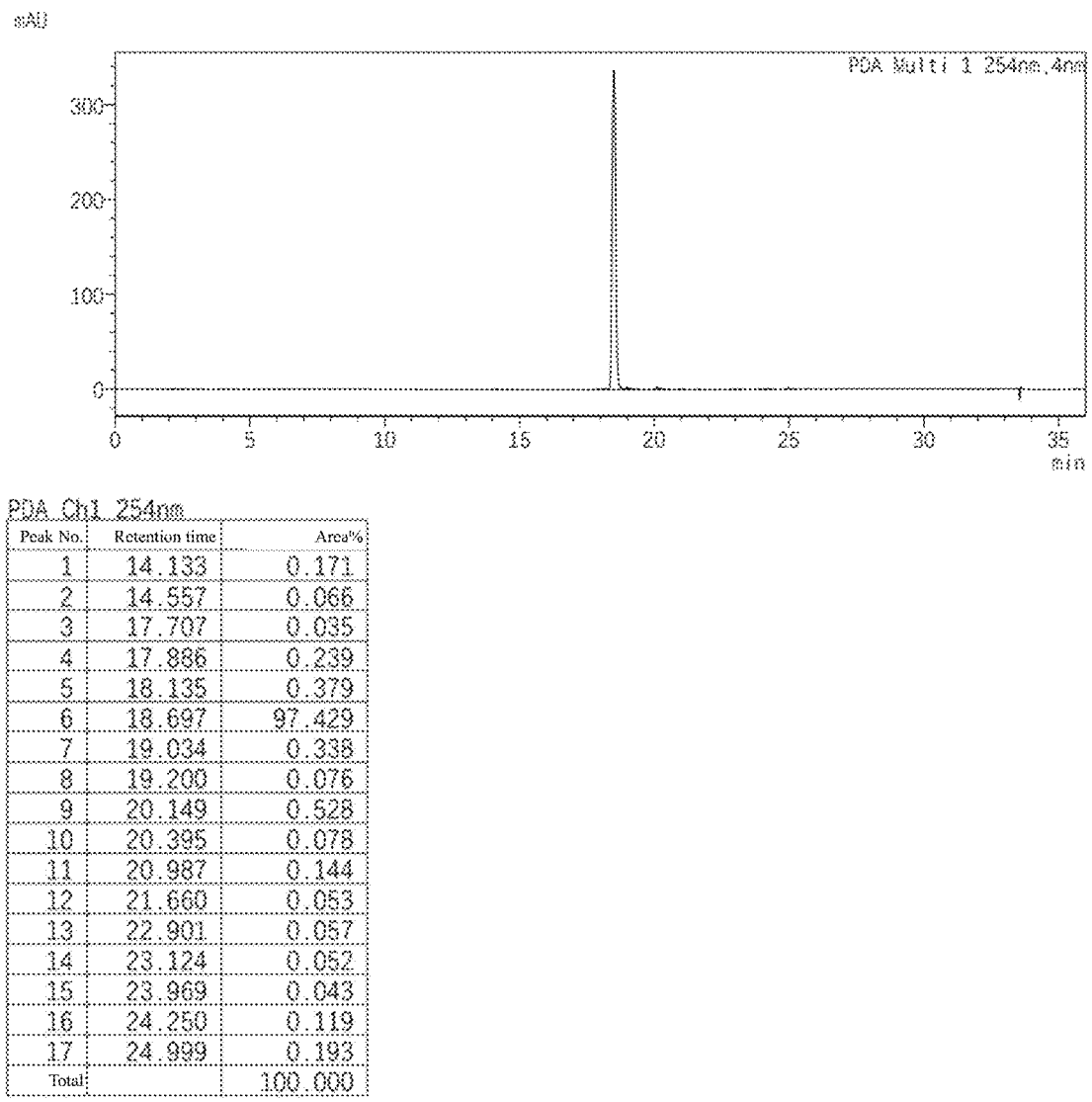
FIG. 5 is a HPLC chromatogram of the compound prepared in Example 10.
Figure 6:
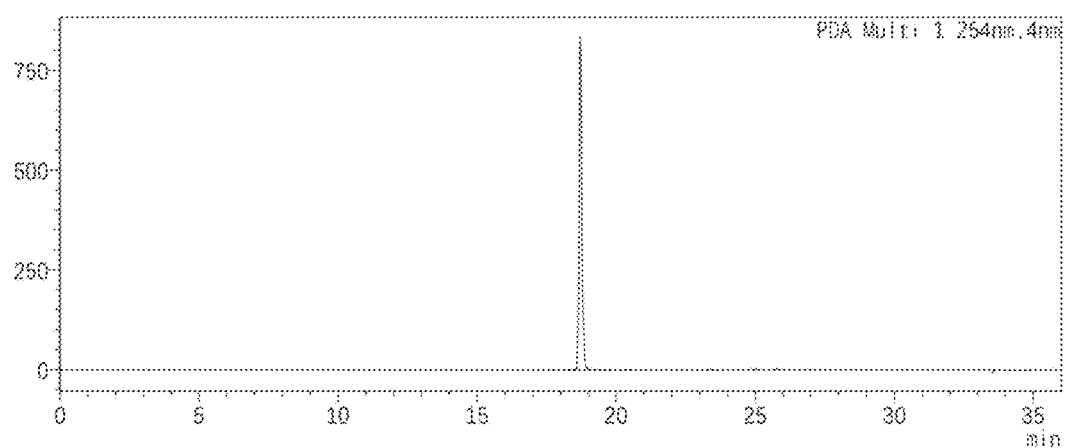
FIG. 6 is a HPLC chromatogram of the compound prepared in Example 13.
Figure 7:
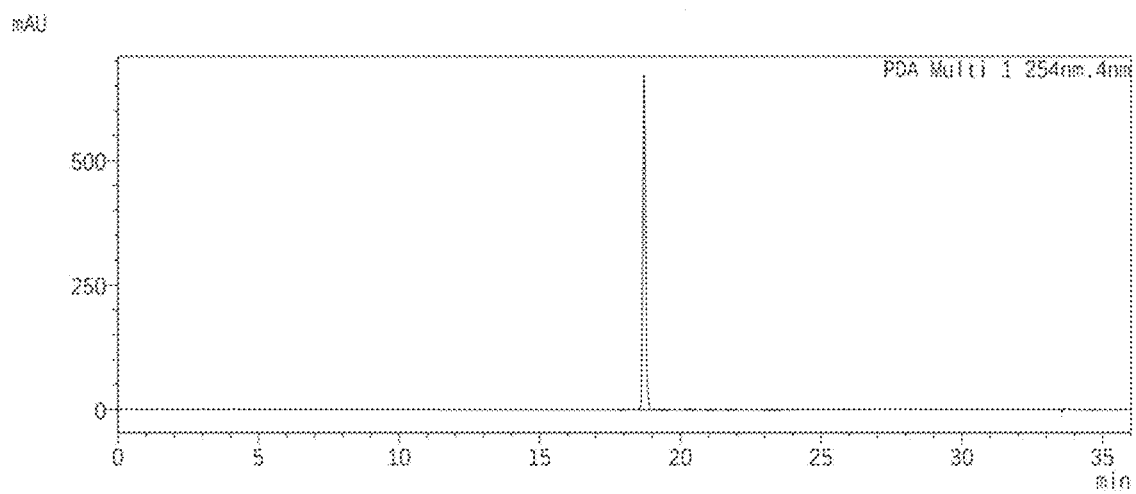
FIG. 7 is a HPLC chromatogram of the compound prepared in Example 14.
Figure 8:
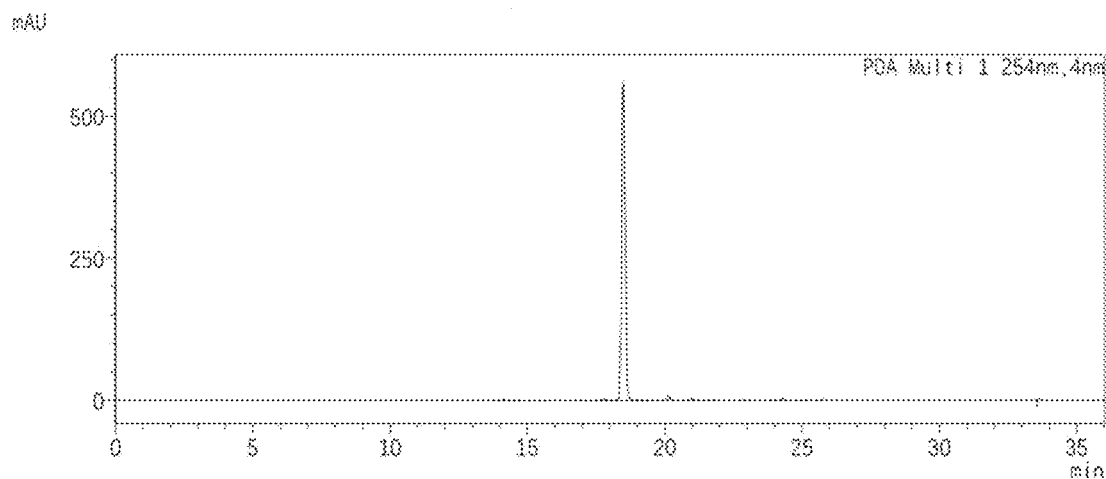
FIG. 8 is a HPLC chromatogram of the compound prepared in Example 19.
Figure 9:
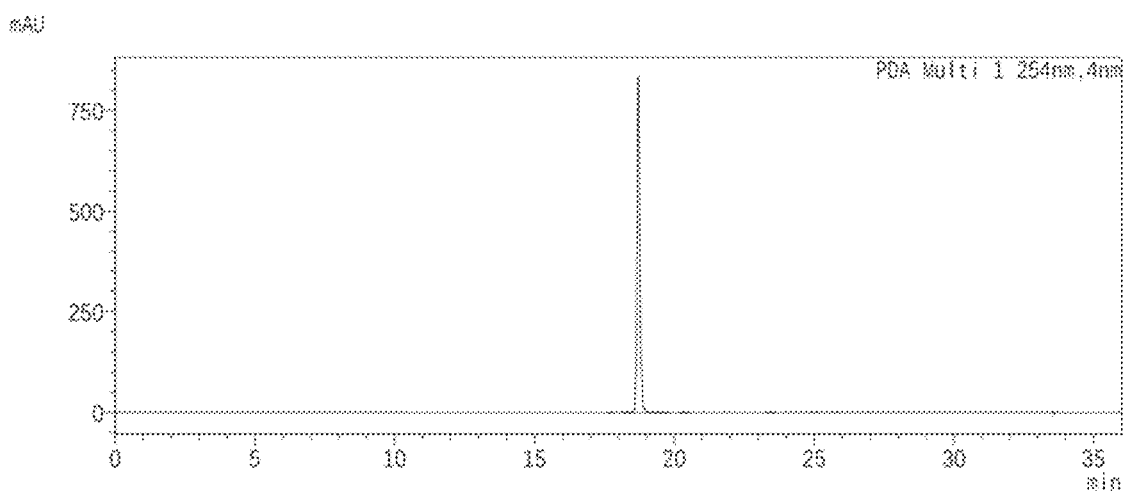
FIG. 9 is a HPLC chromatogram of the compound prepared in Example 23.
Figure 10:
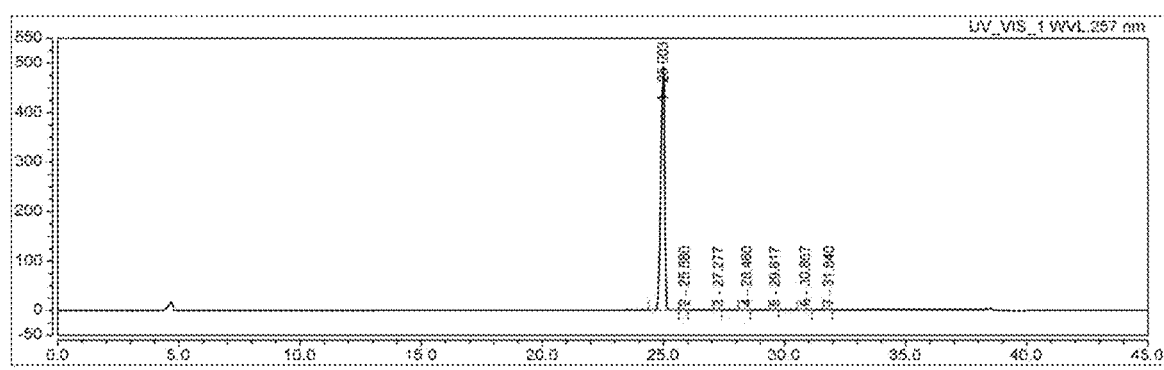
FIG. 10 is a HPLC chromatogram of fumarate salt of the compound prepared in Example 28.

For the purposes of the present invention, the terms used herein have the following meanings, unless otherwise indicated.

The term "co-solvent" means that when a soluble intermolecular complex, association, complex salt or the like can be formed by a sparingly soluble substance and a third substance added in a solvent to increase the solubility of the sparingly soluble substance in the solvent, this third substance is referred to as a co-solvent. Examples of the co-solvent include, but not limited to, dioxane, $C_1$-$C_6$ alkyl ketone, $C_1$-$C_6$ alkyl alcohol, dimethylacetamide, dimethylformamide, acetonitrile, dimethylsulfoxide and/or N-methylpyrrolidone.

The term "halogen", "halogen atom" or "halogenated or halo" refers to fluorine, chlorine, bromine and iodine, in particular to bromine, chlorine or fluorine, preferably chlorine or fluorine.

The term "$C_1$-$C_6$ alkyl" refers to a straight or branched chain alkyl group having a specified number of carbon atoms (e.g., one, two, three, four, five or six carbon atoms), such as methyl, ethyl, n-propyl, isopropyl, n-butyl, isobutyl, sec-butyl, tert-butyl, pentyl, isopentyl, hexyl, 2-methylbutyl, 1-methylbutyl, 1-ethylpropyl, 1,2-dimethylpropyl, neopentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl or 1,2-dimethylbutyl. Generally, the term "alkyl" refers to, if the number of carbon atoms is not specified, a straight or branched chain alkyl group having 1 to 9, in particular 1 to 6, preferably 1 to 4 carbon atoms. In particular, the alkyl has 1, 2, 3, 4, 5 or 6 carbon atoms ("$C_1$-$C_6$ alkyl"), for example, methyl, ethyl, n-propyl, isopropyl, n-butyl, tert-butyl, pentyl, isopentyl, hexyl, 2-methylbutyl, 1-methylbutyl, 1-ethylpropyl, 1,2-dimethylpropyl, neopentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl or 1,2-dimethylbutyl. Preferably, the alkyl has 1, 2 or 3 carbon atoms ("$C_1$-$C_3$ alkyl"), such as methyl, ethyl, n-propyl or isopropyl.

The term "$C_1$-$C_{10}$ alkane" refers to a straight or branched chain alkane having 1 to 10 carbon atoms. It examples include, but not limited to, methane, ethane, n-propane, iso-propane, n-butane, tert-butane, n-pentane, n-hexane, n-heptane, and the like.

The term "$C_3$-$C_6$ cycloalkane" refers to a straight or branched chain alkane having 1 to 10 carbon atoms. It examples include, but not limited to, cyclopropane, cyclobutane, cyclopentane, cyclohexane, and the like.

The term "$C_1$-$C_6$ alkyl ketone" refers to a straight or branched chain alkyl ketone containing 1 to 6 carbon atoms, i.e., a $C_1$-$C_6$ alkyl group having a ketone group (C=O). Its examples include, but not limited to, acetone and methyl isobutyl ketone.

The term "$C_1$-$C_6$ alkyl alcohol" refers to a straight or branched chain alkyl alcohol containing 1 to 6 carbon atoms, i.e., a $C_1$-$C_6$ alkyl group having a hydroxyl group (OH). Its examples include, but not limited to, methanol, ethanol, n-propanol, isopropanol, n-butanol, isobutanol, tert-butanol, n-pentanol, 2-pentanol, 3-pentanol, n-hexanol and the like.

The term "$C_1$-$C_6$ halogenated alkane" refers to a halogen-substituted straight or branched chain alkane containing 1 to 6 carbon atoms, i.e., a $C_1$-$C_6$ alkane group in which one or more hydrogen atoms are replaced with halogen. Its examples include, but not limited to, those selected from the group consisting of dichloromethane, trichloromethane, tetrachloromethane, bromoethane, 1,2-dichloroethane and the like.

The term "$C_1$-$C_6$ alkyl carboxylic acid" refers to a straight or branched chain alkyl carboxylic acid containing 1 to 6 carbon atoms, i.e., a $C_1$-$C_6$ alkyl group having a carboxyl group (—COOH). Its examples include, but not limited to, those selected from the group consisting of formic acid, acetic acid, propionic acid, butyric acid, valeric acid, caproic acid and the like.

The term "di-$C_1$-$C_6$ alkyl ether" refers to a straight or branched chain alkyl ether containing 1 to 6 carbon atoms, i.e., a $C_1$-$C_6$ alkyl group having an ether group (—O—). Its examples include, but not limited to, dimethyl ether, diethyl ether, methyl butyl ether, di-n-propyl ether, di-isopropyl ether, 1,2-epoxyethane, cis-2,3-epoxybutane, trans-2,3-epoxybutane and the like.

The compound mentioned herein may be present in free form, e.g., as a free base or as a free acid or as zwitterion, or may be present in the form of a salt. The salt may be any salt, such as any organic or inorganic addition salt, and in particular any physiologically acceptable organic or inorganic addition salt, commonly used in pharmacy.

For the purposes of the present invention, preferred salts are physiologically acceptable salts of the compound mentioned in the present application. Nevertheless, the preferred salts also include salts which are not suitable for pharmaceutical applications but which can be used, for example, for the isolation or purification of the compound described herein.

The term "physiologically acceptable salt" refers to relatively non-toxic, inorganic or organic acid addition salts of the compound described herein, see, e.g., S. M. Berge et al, "Pharmaceutical Salts", *J. Pharm. Sci.* 1977, 66, 1-19.

The physiologically acceptable salts of the compound mentioned in the present application encompass acid addition salts of inorganic acid, carboxylic acid, and sulfonic acid, for example salts of hydrochloric acid, hydrobromic acid, hydroiodic acid, sulfuric acid, disulfuric acid, sulfamic acid, phosphoric acid and nitric acid, or salts with organic acid, such as formic acid, acetic acid, acetoxyacetic acid, pyruvic acid, trifluoroacetic acid, propionic acid, butyric acid, caproic acid, heptanoic acid, undecanoic acid, dodecanoic acid, benzoic acid, salicylic acid, 2-(4-hydroxybenzoyl)-benzoic acid, camphoric acid, cinnamic acid, cyclopentanepropionic acid, digluconic acid, octanoic acid, 3-hydroxy-2-naphthoic acid, nicotinic acid, pamoic acid, pectinic acid, peroxydisulfuric acid, 3-phenylpropionic acid, pivalic acid, 2-hydroxyethanesulfonic acid, itaconic acid, trifluoromethanesulfonic acid, dodecylsulfuric acid, ethanesulfonic acid, benzenesulfonic acid, p-toluenesulfonic acid, methanesulfonic acid, 2-naphthalenesulfonic acid, naphthalenedisulfonic acid, camphorsulfonic acid, citric acid, tartaric acid, stearic acid, lactic acid, pantothenic acid, mucic acid, succinic acid, oxalic acid, malonic acid, succinic acid, malic acid, adipic acid, alginic acid, maleic acid, fumaric acid, gluconic acid, mandelic acid, ascorbic acid, glucoheptonic acid, glycerophosphoric acid, aspartic acid, sulfosalicylic acid, or thiocyanic acid. Fumarate salt is particularly preferred. Examples of the salts include all possible salts of the compound mentioned herein which are a single salt or any mixture of the salts in any ratio of, e.g., 3:1, 2:1, 1:1 and 1:2.

The term "salt" or "physiologically acceptable salt" used in the present application, in a broad sense, also includes a complex, co-crystal form and the like obtained from the compound mentioned in the present application and the acid mentioned in the present application.

The term "subject" refers to an animal, including but not limited to a primate (e.g., human), monkey, cow, pig, sheep, goat, horse, dog, cat, rabbit, rat or mouse. Particularly, the subject is 0 years old or older, 1 year or older, 2 years old or older, 4 years old or older, 5 years old or older, 10 years old or older, 12 years old or older, 13 years old or older, 15 years old or older, 16 years old or older, 18 years old or older, 20 years old or older, 25 years old or older, 30 years old or older, 35 years old or older, 40 years old or older, 45 years old or older, 50 years old or older, 55 years old or older, 60 years old or older, 65 years old or older, 70 years old or older, 75 years old or older, 80 years old or older, 85 years old or older, 90 years old or older, 95 years old or older, 100 years old or older, or 105 years old or older.

The term "coronavirus" belongs to Coronavirus genus of Coronaviridae family. One variant of coronavirus is a pathogen causing atypical pneumonia. Coronaviruses include, but are not limited to, 2019 novel coronavirus (2019-nCoV or SARS-CoV-2, causing novel coronavirus pneumonia COVID-19), HCoV-229E, HCoV-OC43, HCoV-NL63, HCoV-HKU1, SARS-CoV (causing Severe Acute Respiratory Syndrome), and MERS-CoV (causing Middle East Respiratory Syndrome). The disease caused by coronaviruses is mainly respiratory infection (including severe acute respiratory syndrome (SARS)).

The term "novel coronavirus" refers to 2019 novel coronavirus (2019-nCoV) or severe acute respiratory syndrome coronavirus 2 (SARS-CoV-2) published by International Committee on Taxonomy of Viruses in February 2020. The SARS-CoV-2 and 2019-nCoV have the same meaning in the present application and include all variants of the 2019 novel coronavirus, such as all variants recorded by NCBI or GISAID (Global Initiative on Sharing All Influenza Data), especially important variants with strong transmission, pathogenicity or immune evasion, such as Alpha, Beta, Gamma, Delta, Eta, Iota, Kappa or Lambda variants pointed out by WHO, and other important variants pointed out subsequently.

In a first aspect of the present invention, the present invention provides the following particular embodiments and/or any combination thereof.

In a particular embodiment, in the composition of the present invention, the compound of formula (I) or a physiologically acceptable salt has a HPLC purity of ≥95%; preferably, the compound of formula (I) or a physiologically acceptable salt has a HPLC purity of ≥98.5%.

The term "HPLC purity" refers to the HPLC content of a compound (e.g., a compound of formula (I) or a physiologically acceptable salt as defined herein) (i.e., the percentage of peak area of the compound to the peak area of all peaks in HPLC chromatogram).

In a particular embodiment, single impurity content in the composition of the present invention is <1%. Preferably, single impurity content in the composition is <0.5%, 0.2%, 0.1% or 0.05%. Particularly, the single impurity is the compound (6E)-6-[(6-chloro-1-methyl-1H-indazol-5-yl)imino]-3-[(1-methyl-1H-1,2,4-triazol-3-yl)methyl]-1-(2,4,5-trifluorobenzyl)-1,3,5-triazinane-2,4-dione (hereinafter sometimes referred to as "compound A"),

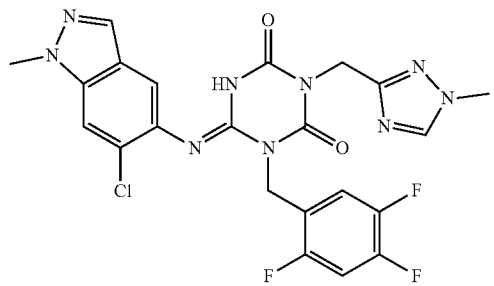

and compound A has a content of <0.2%, preferably <0.1%, and more preferably <0.05%. Particularly, the composition of the present invention does not comprise an impurity compound such as compound A, i.e., (6E)-6-[(6-chloro-1-methyl-1H-indazol-5-yl)imino]-3-[(1-methyl-1H-1,2,4-triazol-3-yl)methyl]-1-(2,4,5-trifluorobenzyl)-1,3,5-triazinane-2,4-dione. In the present invention, expression such as "the composition does not comprise an impurity compound . . . " means that the impurity compound is undetectable within the detection limits of HPLC.

The term "single impurity content" refers to the HPLC content of single impurity (e.g., compound A as defined herein) (i.e., the percentage of peak area of a single impurity to the peak area of all peaks in the HPLC chromatogram). Similarly, the term "content" refers to HPLC content, i.e., content measured by HPLC.

In a particular embodiment, in formula (I), $R_1$ and $R_2$ are each independently methyl.

In a particular embodiment, in formula (I), substituent X on the indazole ring may be identical to or different from substituent(s) X on the phenyl ring in the benzyl group. Particularly, substituent X on the indazole ring is fluorine or chlorine, preferably chlorine; and/or substituent(s) X on the phenyl ring in the benzyl group is/are each independently fluorine or chlorine, preferably fluorine. In a particular embodiment, in formula (I), n is 2, 3 or 4. Particularly, when n is 3, substituents X are substituents at 2,3,4-position, substituents at 2,3,6-position, substituents at 2,4,5-position, substituents at 2,5,6-position, substituents at 3,4,5-position, substituents at 3,5,6-position or substituents at 4,5,6-position, preferably substituents at 2,4,5-position. More particularly, when n is 3, substituents X on the phenyl rings in the benzyl groups are each independently identical or different, preferably identical. Still more particularly, when n is 3, substituents X are 2,3,4-trifluoro, 2,3,6-trifluoro, 2,4,5-trifluoro, 2,5,6-trifluoro, 3,4,5-trifluoro, 3,5,6-trifluoro or 4,5,6-trifluoro, preferably 2,4,5-trifluoro.

In a particular embodiment, the compound of formula (I) is

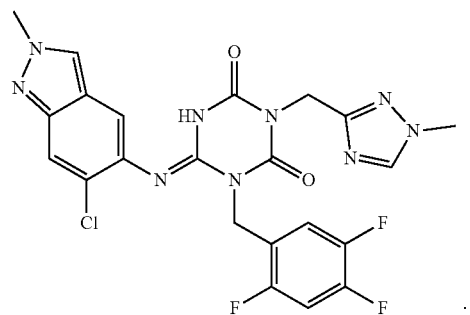

In a particular embodiment, the physiologically acceptable salt of the compound of formula (I) is fumarate salt of the compound of formula (I).

In a particular embodiment, the composition of the present invention is a white solid.

In a particular embodiment, in the composition of the present invention, the sum of the weight percentages of the compound of formula (I) or a physiologically acceptable salt as defined herein and of the single impurity as defined herein (such as compound A) in the composition of the present invention is 100%. Alternatively, in a particular embodiment, the composition of the present invention consists of the compound of formula (I) or a physiologically acceptable salt as defined herein and the single impurity (such as compound A) as defined herein.

In a particular embodiment, the composition of the present invention is obtained from the method for preparing and/or purifying defined below.

In a second aspect of the present invention, the present invention provides the following particular embodiments and/or any combination thereof.

In a particular embodiment, the composition comprising a salt of the compound of formula (I) is prepared by a method comprising the following step:
  performing a salt-forming reaction of the composition comprising the compound of formula (I) with an acid.

Particularly, the salt of the compound of formula (I) can be fumarate, maleate or tosylate salt. More particularly, the salt of the compound of formula (I) is fumarate salt.

Particularly, in the composition comprising a salt (such as fumarate salt) of the compound of formula (I), the salt (such as fumarate salt) of the compound of formula (I) has a HPLC purity of 99.0%; preferably, the salt (such as fumarate salt) of the compound of formula (I) has a HPLC purity of 99.8%.

Particularly, in the composition comprising a salt (such as fumarate salt) of the compound of formula (I), single impurity content is <0.1%.

Particularly, in the composition comprising a salt (such as fumarate salt) of the compound of formula (I), the compound of formula (I) and the acid (such as fumaric acid) are in a ratio in the range of 3:1 to 1:2, preferably in the range of 1:1 to 1:2, for example 3:1, 2:1, 1:1 or 1:2, preferably 1:1 to 1:2.

Particularly, the salt of the compound of formula (I) can be a monomorph or a polymorph; or, the salt of the compound of formula (I) can be a complex or co-crystal form of the compound of formula (I) and the acid. For example, the fumarate salt of the compound of formula (I) is a monomorph or a polymorph; or, the fumarate salt of the compound of formula (I) can be a complex or co-crystal form of the compound of formula (I) and the fumaric acid.

Particularly, the acid may be fumaric acid, maleic acid or toluenesulfonic acid.

Particularly, the salt-forming reaction is performed in the presence of a solvent. More particularly, the solvent is a conventional organic solvent, such as $C_1$-$C_6$ alkyl ketone, $C_1$-$C_6$ alkyl alcohol, $C_1$-$C_{10}$ alkane, $C_3$-$C_6$ cycloalkane, di-$C_1$-$C_6$ alkyl ether, $C_1$-$C_6$ halogenated alkane, dioxane, ethylene glycol dimethyl ether, acetonitrile, toluene, ethyl formate, ethyl acetate, isopropyl acetate, butyl formate, dichloromethane, chloroform, dimethylsulfoxide, 4-methyl-2-pentanone, and/or tetrahydrofuran, for example, particularly, ethyl acetate, isopropyl acetate, acetone, 1,4-dioxane, ethylene glycol dimethyl ether, methanol, tetrahydrofuran, acetonitrile, dichloromethane, chloroform, toluene or ethanol.

Particularly, the salt-forming reaction is performed at room temperature (e.g., 20-25° C.).

Particularly, the compound of formula (I) is as defined herein. For example, the compound of formula (I) is

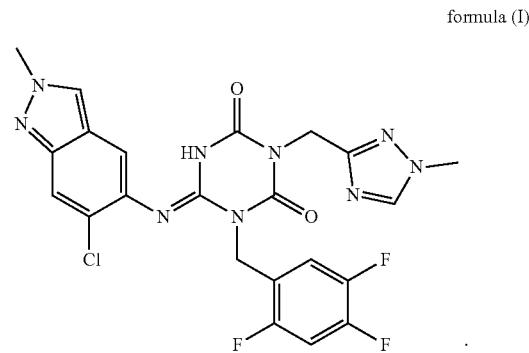

formula (I)

In a third aspect of the present invention, the present invention provides the following particular embodiments and/or any combination thereof.

In a particular embodiment, the method for treating or preventing a disease caused by a coronavirus according to the present invention comprises administering a therapeutically effective amount of the composition according to the present invention to a subject.

In a particular embodiment, the coronavirus is a novel coronavirus.

In a particular embodiment, the subject is a human, e.g., a child (e.g., a human of 0-18 years old or 0-14 years old), an adult (e.g., a human of 19-59 years old) or an elderly human (e.g., a human of 60 years old or older).

The term "therapeutically effective amount" refers to an amount of the composition or the compound of formula (I) as defined herein that causes a biological or medical response in a subject, or ameliorates symptoms, alleviates disorders, slows or delays disease progression, prevents diseases or the like, as compared to a subject that does not receive that amount. The term also includes within its scope an amount effective to enhance normal physiological function.

In a further aspect of the present invention, it provides a method for purifying a composition comprising the compound of formula (I), in which the method comprises the following steps: (ii) dispersing a to-be-purified composition comprising the compound of formula (I) in one or more solvents, optionally heating, stirring and/or cooling, followed by filtrating to obtain the composition comprising the compound of formula (I);

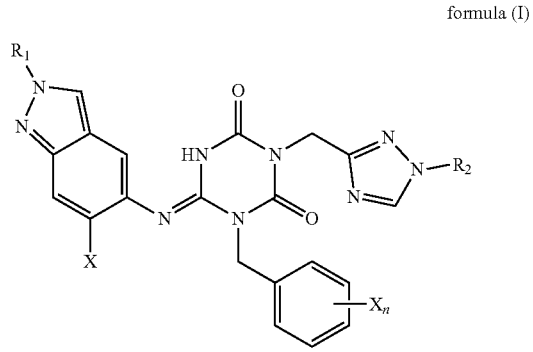

formula (I)

wherein

R₁ and R₂ are each independently $C_1$-$C_6$ alkyl;

X is halogen; and n is 1 to 5.

Particularly, the method for purifying comprises the following steps:

(i) recrystallizing a to-be-purified composition comprising the compound of formula (I) in a mixed solvent; and (ii) dispersing solid obtained in the step (i) in one or more solvents, optionally heating, stirring and/or cooling, followed by filtrating to obtain the composition comprising the compound of formula (I);

or (ii) dispersing a to-be-purified composition comprising the compound of formula (I) in one or more solvents, optionally heating, stirring and/or cooling, followed by filtrating to obtain a solid; and (i) recrystallizing the solid obtained in the step (ii) in a mixed solvent.

More particularly, the step (i) and/or step (ii) further comprises drying the solid, preferably drying it in vacuum.

More particularly, the step (i) further comprises filtering the solid obtained from recrystallization, preferably filtering it by suction.

More particularly, the step (i) and/or step (ii) is performed one or more times, preferably one or two times.

More particularly, in the step (i), the mixed solvent is a mixture of any two of $C_1$-$C_6$ halogenated alkane, $C_1$-$C_6$ alkyl carboxylic acid and di-$C_1$-$C_6$ alkyl ether, preferably a mixture of $C_1$-$C_6$ halogenated alkane and di-$C_1$-$C_6$ alkyl ether or a mixture of $C_1$-$C_6$ alkyl carboxylic acid and di-$C_1$-$C_6$ alkyl ether. Preferably, the volume (in mL) of the mixed solvent and the weight (in g) of the to-be-purified composition comprising the compound of formula (I) are in a ratio in the range of 12:1 to 1:1, preferably in the range of 8:1 to 2:1. More particularly, in the step (i), two solvents (such as $C_1$-$C_6$ halogenated alkane and di-$C_1$-$C_6$ alkyl ether; or, $C_1$-$C_6$ alkyl carboxylic acid and di-$C_1$-$C_6$ alkyl ether) in the mixed solvent are in a volume ratio in the range of 5:1 to 1:5, preferably in the range of 4.5:1 to 1:4.5, more preferably in the range of 4:1 to 1:4, and most preferably in the range of 3:1 to 1:3.

More particularly, in the step (ii), the heating is performed at a temperature in the range of 40-80° C., preferably 50-70° C.

More particularly, in the step (ii), the cooling is performed at a temperature in the range of 0-35° C., preferably in the range of 10-30° C.

More particularly, in the step (ii), the solvent is water, $C_1$-$C_6$ alkyl alcohol, di-$C_1$-$C_6$ alkyl ether and/or $C_1$-$C_6$ alkyl ketone. Preferably, when the solvent is one solvent, it is water, $C_1$-$C_6$ alkyl ketone, or $C_1$-$C_6$ alkyl alcohol, preferably $C_1$-$C_6$ alkyl ketone or $C_1$-$C_6$ alkyl alcohol; when the solvent is a plurality of solvents, it can be a mixture of two solvents, such as a mixture of $C_1$-$C_6$ alkyl alcohol and di-$C_1$-$C_6$ alkyl ether, or a mixture of water and $C_1$-$C_6$ alkyl ketone, preferably, two solvents (such as $C_1$-$C_6$ alkyl alcohol and di-$C_1$-$C_6$ alkyl ether; or, water and $C_1$-$C_6$ alkyl ketone) are in a volume ratio in the range of 5:1 to 1:5, preferably in the range of 4.5:1 to 1:4.5, more preferably in the range of 4:1 to 1:4, and most preferably in the range of 3:1 to 1:3. Preferably, the volume (in mL) of the solvent and the weight (in g) of the to-be-purified composition comprising the compound of formula (I) are in a ratio in the range of 8:1 to 1:1, preferably in the range of 6:1 to 2:1.

Particularly, the to be purified composition comprising the compound of formula (I) is obtained from the method known in the prior art or obtained from the method for preparing defined below. Particularly, the compound of formula (I) is as defined herein. For example, in the compound of formula (I), R₁, R₂, X and n are as defined herein. For example, the compound of formula (I) is

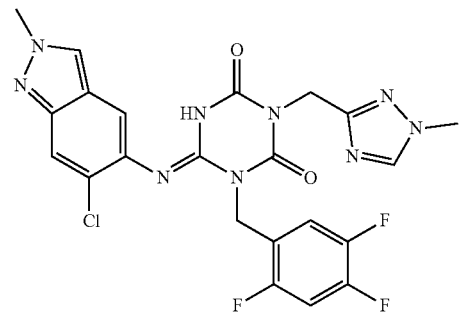

Particularly, as the product, the composition comprising the compound of formula (I) is the composition comprising the compound of formula (I) according to the present invention that is as defined in the present application. Particularly, in the composition as the product, the compound of formula (I) has a HPLC purity of ≥95.0%. Particularly, in the composition as the product, a single impurity content is <0.5%, 0.2%, 0.1% or 0.05%. Particularly, as the product, the composition is a white solid.

The method for purifying a composition comprising the compound of formula (I) described in this application also apply to purification of the compound of formula (I).

In another aspect of the present invention, it provides a method for preparing a composition comprising the compound of formula (I), in which the method comprises the following steps:

(a) reacting a compound of formula (II)

formula (II)

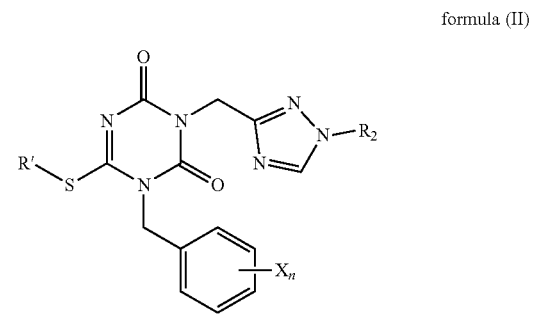

wherein,

R' is $C_1$-$C_6$ alkyl;

R₂, X and n are as defined in formula (I);

with a compound of formula (III)

formula III

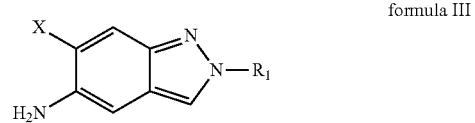

wherein, $R_1$ and X are as defined in formula (I);

in the presence of a base added in portions and/or a co-solvent to obtain the composition comprising the compound of formula (I);

formula (I)

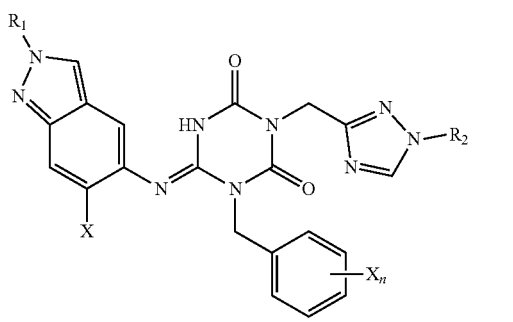

wherein $R_1$ and $R_2$ are each independently $C_1$-$C_6$ alkyl;

X is halogen; and n is 1 to 5.

Particularly, the compound of formula (II) is synthesized by the following steps:

(b) reacting a compound of formula (IV)

formula IV

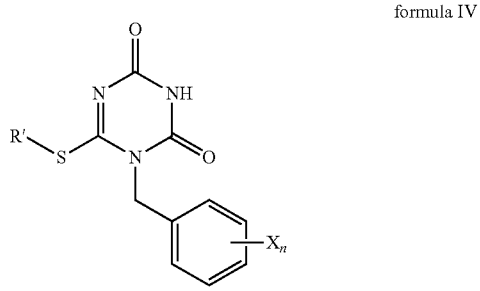

wherein,

R', X and n are as defined in formula (II);

with a compound of formula (V) or a salt thereof formula (V)

wherein, $R_2$ and X are as defined in formula (II);

to obtain the compound of formula (II).

Particularly, the method for preparing comprises the following step: reacting a compound of formula (II) with a compound of formula (III) in the presence of a co-solvent to obtain the composition comprising the compound of formula (I); alternatively, the method for preparing comprises the following step: reacting a compound of formula (II) with a compound of formula (III) in the presence of a base added in portions to obtain the composition of the present invention comprising the compound of formula (I). More particularly, the method for preparing comprises the following step: reacting a compound of formula (II) with a compound of formula (III) in the presence of a co-solvent and a base added in portions to obtain the composition comprising the compound of formula (I).

Particularly, the co-solvent is selected from the group consisting of dioxane, $C_1$-$C_6$ alkyl ketone, $C_1$-$C_6$ alkyl alcohol, dimethylacetamide, dimethylformamide, acetonitrile, dimethylsulfoxide, N-methylpyrrolidone, and any mixture thereof.

Particularly, the co-solvent is anhydrous.

Particularly, the co-solvent is a mixture of water and another solvent selected from the group consisting of dioxane, $C_1$-$C_6$ alkyl ketone, $C_1$-$C_6$ alkyl alcohol, dimethylacetamide, dimethylformamide, acetonitrile, dimethylsulfoxide, N-methylpyrrolidone, and any mixture thereof. Preferably, water and another solvent may be mixed in any ratio.

Particularly, the step (a) is performed in a solvent, for example an organic solvent which can be selected from the group consisting of ethyl acetate, methyl formate, di-$C_1$-$C_6$ alkyl ether, tetrahydrofuran, toluene, and a mixture thereof, preferably tetrahydrofuran. Preferably, the co-solvent and the solvent are in a volume ratio in the range of 1:15 to 1:2, preferably in the range of 1:9 to 1:3, and more preferably in the range of 1:7 to 1:4.

Particularly, the volume of the co-solvent is 5% to 35%, preferably 10% to 30%, and more preferably 15% to 25% of the total volume of reaction system in the step (a).

Particularly, the step (a) is performed in the presence or absence of a catalyst. Particularly, when a catalyst is present, the compound of formula (II) and the catalyst are in a molar ratio in the range of 1:1 to 1:3, e.g., 1:2. Particularly, when a catalyst is present, the catalyst is a base, such as lithium hexamethyldisilazide (LHMDS), potassium tert-butoxide or lithium diisopropylamide.

Particularly, the base added in portions is the base added in two or more portions (e.g., two, three or more portions), wherein each of the portions can be the same or different. Preferably, the base added in portions is the base added in portions, in which each of the portions can be the same or different and the portions can be two or more portions added at different time points. For example, the portions are two, three or more portions added at different time points, in which each of the portions can be the same or different (for example, when the portions are two portions, each of the portions is different, particularly the portion added firstly is double or a half of the portion added secondly; when the portions are three portions, each of the portions is the same), and/or each of the portions is added at a time interval of at least 5 min, 10 min, 15 min, 20 min, 25 min, 26 min, 27 min, 28 min, 29 min or 30 min.

Particularly, the base is lithium hexamethyldisilazide (LHMDS), potassium tert-butoxide or lithium diisopropylamide. More particularly, the compound of formula (II) and the base are in a molar ratio in the range of 1:1 to 1:3, e.g., 1:2. More particularly, the base is added dropwise, for example, the base is added slowly dropwise.

Particularly, step (a) is performed at a temperature of 0-55° C.; preferably, step (a) is performed firstly at a low temperature (0-5° C.) and subsequently at an elevated temperature (e.g., room temperature or higher, such as 20-25° C. or higher). Alternatively, step (a) is preferably performed at an elevated temperature (e.g., 20-30° C.).

Particularly, the compound of formula (II) and the compound of formula (III) are in a molar ratio in the range of 1:1 to 1:1.5, preferably in the range of 1:1.1 to 1:1.4, such as 1:1.2 or 1:1.3.

Particularly, the method for preparing further comprises a purification step. More particularly, the purification step is a column chromatography and/or recrystallization step. More particularly, the purification step is the method for purifying the composition as defined herein. More particularly, the column chromatography is performed by using a mixed solvent of $C_1$-$C_6$ halogenated alkane and $C_1$-$C_6$ alkyl alcohol, preferably, the mixed solvent is gradient, and more preferably, the volume percentage of the $C_1$-$C_6$ alkyl alcohol in the mixed solvent is 0-20%. More particularly, the recrystallization step is performed in a mixed solvent of water and $C_1$-$C_6$ alkyl ketone. Preferably, two solvents (such as $C_1$-$C_6$ halogenated alkane and $C_1$-$C_6$ alkyl alcohol) in the mixed solvent are in a volume ratio in the range of 5:1 to 1:5, preferably in the range of 4.5:1 to 1:4.5, more preferably in the range of 4:1 to 1:4, and most preferably in the range of 3:1 to 1:3.

Particularly, the compound of formula (I) is as defined herein. For example, in the compound of formula (I), $R_1$, $R_2$, X and n are as defined herein. For example, the compound of formula (I) is

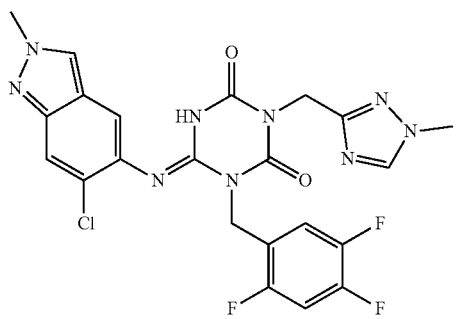

Particularly, as the product, the composition comprising the compound of formula (I) is the composition comprising the compound of formula (I) according to the present invention that is as defined in the present application. Particularly, in the composition as the product, the compound of formula (I) has a HPLC purity of ≥95.0%, particularly ≥98.5%. Particularly, in the composition as the product, single impurity content is <1%, more particularly <0.5%, 0.2%, 0.1% or 0.05%.

Particularly, as the product, the composition is a white solid.

The method for preparing a composition comprising the compound of formula (I) described in this application also apply to preparation of the compound of formula (I).

In other aspects of the present invention, it provides a composition comprising fumarate salt of the compound of formula (I), wherein the fumarate salt of the compound of formula (I) has a HPLC purity of ≥99.0%; preferably, the fumarate salt of the compound of formula (I) has a HPLC purity of ≥99.8%. More preferably, in the fumarate salt of the compound of formula (I), single impurity content is <0.1%. Particularly, the fumarate salt of the compound of formula (I) is obtained by salt-forming reaction of the compound of the formula (I) with fumaric acid. More particularly, the salt-forming reaction is as defined herein. Particularly, the fumarate salt of the compound of formula (I) is as defined herein. For example, in the fumarate salt of the compound of formula (I), the compound of formula (I) and fumaric acid are in a ratio of 3:1, 2:1, 1:1 or 1:2, preferably 1:1.

The method for preparing and/or purifying according to the present invention gives the composition of the present invention with high yield, in which the composition of the present invention comprises compound 1 with high purity, has good fluidity and anti-caking property, and is suitable for preparing a salt (e.g., fumarate salt) of the target compound (i.e., compound 1) with higher purity (for example, ≥99% (HPLC) purity), thereby meeting pharmaceutical standards while facilitating formulation development. In addition, the method for preparing and/or purifying according to the present invention gives the composition with high yield, the compound of formula (I) having high purity comprised in the obtained composition, and lower production cost, and is more environmentally friendly and more suitable for industrial production. Furthermore, the method according to the present invention may remove at least one impurity compound (such as compound A) which is difficult to be removed by the method(s) in the prior art, so that the product is more suitable for pharmaceutical use and is more favorable for formulation development requirements.

The respective embodiments or different preferred embodiments described herein may be combined in any combination, unless otherwise indicated.

The present invention is illustrated below by way of examples, but it should not be construed that the scope of the subject matter of the present invention is limited to the following examples. All techniques implemented based on the above description of the present disclosure fall within the scope of the present disclosure. The compounds or reagents used in the following examples are commercially available or may be prepared by conventional methods known to those skilled in the art; the laboratory instruments used are commercially available.

EXAMPLES

All commercial reagents and solvents were not further purified. The reaction was monitored by thin layer chromatography or analytical liquid chromatography/mass spectrometry (LC/MS), and the thin layer chromatography was performed on the Yantai Jiangyou silica gel plate (HSGF254). The column chromatography was completed by silica gel prepackaged by Dingkang silica gel and a chromatographic column. Purity was measured by HPLC method on Agilent Technologies 1260 Infinity, and test conditions were as follows: chromatographic column: a C18 column; injection volume: 10 µL; fluidity: water+acetonitrile; 95:5 for 25 min→10:90 for 6 min→95:5 for 5 min; flow rate: 1.0 mL/min; column temperature: 30° C.; detection wavelength: 254 nm.

Preparation Examples

Comparative Example 1

To a solution of 6-ethylthio-3-[(1-methyl-1H-1,2,4-triazol-3-yl)methyl]-1-(2,4,5-trifluorobenzyl)-1,3,5-triazine-2,4(1H,3H)-dione (300 mg, 0.727 mmol) and 6-chloro-2-methyl-2H-indazol-5-amine (172 mg, 0.946 mmol) in THF (6 mL) was dropwise added LHMDS (1M in THF, 1.46 mL, 1.46 mmol) at 0° C. The reaction mixture was stirred at 0° C. for 2.5 h, and then reacted at room temperature for 40 min. The reaction system was quenched with aqueous NH₄Cl solution, and the aqueous layer was extracted with EtOAc. The organic layer was washed with brine, dried over MgSO₄, and concentrated under reduced pressure to obtain a brown solid (6E)-6-[(6-chloro-2-methyl-2H-indazol-5-yl)imino]-3-[(1-methyl-1H-1,2,4-triazol-3-yl)methyl]-1-(2,4,5-trifluorobenzyl)-1,3,5-triazinane-2,4-dione (146.0 mg, yield: 38.3%, purity: 80.1%).

Comparative Example 2

To a solution of 6-ethylthio-3-[(1-methyl-1H-1,2,4-triazol-3-yl)methyl]-1-(2,4,5-trifluorobenzyl)-1,3,5-triazine-2,4(1H,3H)-dione (300 mg, 0.727 mmol) and 6-chloro-2-methyl-2H-indazol-5-amine (172 mg, 0.946 mmol) in THF (6 mL) was dropwise added LHMDS (1M in THF, 1.46 mL, 1.46 mmol) at 0° C. The reaction mixture was stirred at 0° C. for 2.5 h, and then reacted at room temperature for 40 min. The reaction system was quenched with aqueous NH₄Cl solution, and the aqueous layer was extracted with EtOAc. The organic layer was washed with brine, dried over MgSO₄, and concentrated under reduced pressure. The residue was purified by silica gel column chromatography (CHCl₃/MeOH gradient, 0-20% MeOH). The solid was solidized with acetone/H₂O (volume ratio: 1:1) to obtain a pale brown solid (6E)-6-[(6-chloro-2-methyl-2H-indazol-5-yl)imino]-3-[(1-methyl-1H-1,2,4-triazol-3-yl)methyl]-1-(2,4,5-trifluorobenzyl)-1,3,5-triazinane-2,4-dione (95.3 mg, yield: 25.0%, purity: 86.2%).

Example 1

A solution of 6-ethylthio-3-[(1-methyl-1H-1,2,4-triazol-3-yl)methyl]-1-(2,4,5-trifluorobenzyl)-1,3,5-triazine-2,4(1H,3H)-dione (300 mg, 0.727 mmol) and 6-chloro-2-methyl-2H-indazol-5-amine (172 mg, 0.946 mmol) in THF (6 mL) was firstly added dropwise with LHMDS (1M in THF, 0.97 mL, 0.97 mmol) at 0° C., and the reaction mixture was stirred for 30 min and then added dropwise with LHMDS (1M in THF, 0.49 mL, 0.49 mmol). The reaction mixture was stirred at 0° C. for 2.5 h, and then reacted at room temperature for 40 min. The reaction system was quenched with aqueous NH₄Cl solution, and the aqueous layer was extracted with EtOAc. The organic layer was washed with brine, dried over MgSO₄, and concentrated under reduced pressure to obtain a yellow solid (6E)-6-[(6-chloro-2-methyl-2H-indazol-5-yl)imino]-3-[(1-methyl-1H-1,2,4-triazol-3-yl)methyl]-1-(2,4,5-trifluorobenzyl)-1,3,5-triazinane-2,4-dione (296.6 mg, yield: 77.8%, purity: 90.2%).

Example 2

A solution of 6-ethylthio-3-[(1-methyl-1H-1,2,4-triazol-3-yl)methyl]-1-(2,4,5-trifluorobenzyl)-1,3,5-triazine-2,4(1H,3H)-dione (300 mg, 0.727 mmol) and 6-chloro-2-methyl-2H-indazol-5-amine (172 mg, 0.946 mmol) in THF (6 mL) was firstly added dropwise with LHMDS (1M in THF, 0.49 mL, 0.49 mmol) at 0° C., and the reaction mixture was stirred for 30 min and then added dropwise with LHMDS (1M in THF, 0.97 mL, 0.97 mmol). The reaction mixture was stirred at 0° C. for 2.5 h, and then reacted at room temperature for 40 min. The reaction system was quenched with aqueous NH₄Cl solution, and the aqueous layer was extracted with EtOAc. The organic layer was washed with brine, dried over MgSO₄, and concentrated under reduced pressure to obtain a yellow solid (6E)-6-[(6-chloro-2-methyl-2H-indazol-5-yl)imino]-3-[(1-methyl-1H-1,2,4-triazol-3-yl)methyl]-1-(2,4,5-trifluorobenzyl)-1,3,5-triazinane-2,4-dione (299.2 mg, yield: 78.5%, purity: 90.6%).

Example 3

A solution of 6-ethylthio-3-[(1-methyl-1H-1,2,4-triazol-3-yl)methyl]-1-(2,4,5-trifluorobenzyl)-1,3,5-triazine-2,4(1H,3H)-dione (300 mg, 0.727 mmol) and 6-chloro-2-methyl-2H-indazol-5-amine (172 mg, 0.946 mmol) in THF (6 mL) was firstly added dropwise with LHMDS (1M in THF, 0.49 mL, 0.49 mmol) at 0° C., the reaction mixture was stirred for 30 min and then added dropwise with LHMDS (1M in THF, 0.49 mL, 0.49 mmol), and the reaction mixture was stirred for another 30 min and then added dropwise with LHMDS (1M in THF, 0.49 mL, 0.49 mmol). The reaction mixture was stirred at 0° C. for 2.5 h, and then reacted at room temperature for 40 min. The reaction system was quenched with aqueous NH₄Cl solution, and the aqueous layer was extracted with EtOAc. The organic layer was washed with brine, dried over MgSO₄, and concentrated under reduced pressure to obtain a yellow solid (6E)-6-[(6-chloro-2-methyl-2H-indazol-5-yl)imino]-3-[(1-methyl-1H-1,2,4-triazol-3-yl)methyl]-1-(2,4,5-trifluorobenzyl)-1,3,5-triazinane-2,4-dione (301.5 mg, yield: 79.1%, purity: 91.9%).

Example 4

A solution of 6-ethylthio-3-[(1-methyl-1H-1,2,4-triazol-3-yl)methyl]-1-(2,4,5-trifluorobenzyl)-1,3,5-triazine-2,4(1H,3H)-dione (300 mg, 0.727 mmol) and 6-chloro-2-methyl-2H-indazol-5-amine (172 mg, 0.946 mmol) in THF (6 mL) was firstly added dropwise with LHMDS (1M in THF, 0.49 mL, 0.49 mmol) at 20-30° C., the reaction mixture was stirred for 30 min and then added dropwise with LHMDS (1M in THF, 0.49 mL, 0.49 mmol), and the reaction mixture was stirred for another 30 min and then added dropwise with LHMDS (1M in THF, 0.49 mL, 0.49 mmol). The reaction mixture was stirred at 20-30° C. for 3.7 h. The reaction system was quenched with aqueous NH₄Cl solution, and the aqueous layer was extracted with EtOAc. The organic layer was washed with brine, dried over MgSO₄, and concentrated under reduced pressure to obtain a yellow solid (6E)-6-[(6-chloro-2-methyl-2H-indazol-5-yl)imino]-3-[(1-methyl-1H-1,2,4-triazol-3-yl)methyl]-1-(2,4,5-trifluorobenzyl)-1,3,5-triazinane-2,4-dione (303.1 mg, yield: 79.5%, purity: 92.8%).

Example 5

To a solution of 6-ethylthio-3-[(1-methyl-1H-1,2,4-triazol-3-yl)methyl]-1-(2,4,5-trifluorobenzyl)-1,3,5-triazine-2,4(1H,3H)-dione (300 mg, 0.727 mmol) and 6-chloro-2-methyl-2H-indazol-5-amine (172 mg, 0.946 mmol) in THF (6 mL) was dropwise added LHMDS (1M in THF, 1.46 mL, 1.46 mmol) at 0° C. The reaction mixture was stirred at 0° C. for 2.5 h, then stirred at room temperature for 40 min, and added with 1.2 mL of isopropanol and stirred until the reaction was substantially completed. The reaction system was quenched with aqueous NH₄Cl solution, and the aqueous layer was extracted with EtOAc. The organic layer was washed with brine, dried over MgSO₄, and concentrated under reduced pressure to obtain a yellow solid (6E)-6-[(6-chloro-2-methyl-2H-indazol-5-yl)imino]-3-[(1-methyl-1H-

1,2,4-triazol-3-yl)methyl]-1-(2,4,5-trifluorobenzyl)-1,3,5-triazinane-2,4-dione (300.8 mg, yield: 78.9%, purity: 92.5%).

Example 6

To a solution of 6-ethylthio-3-[(1-methyl-1H-1,2,4-triazol-3-yl)methyl]-1-(2,4,5-trifluorobenzyl)-1,3,5-triazine-2,4(1H,3H)-dione (300 mg, 0.727 mmol) and 6-chloro-2-methyl-2H-indazol-5-amine (172 mg, 0.946 mmol) in THF (6 mL) was dropwise added LHMDS (1M in THF, 1.46 mL, 1.46 mmol) at 0° C. The reaction mixture was stirred at 0° C. for 2.5 h, then stirred at room temperature for 40 min, and added with 1.2 mL of acetone and stirred until the reaction was substantially completed. The reaction system was quenched with aqueous NH$_4$Cl solution, and the aqueous layer was extracted with EtOAc. The organic layer was washed with brine, dried over MgSO$_4$, and concentrated under reduced pressure to obtain a yellow solid (6E)-6-[(6-chloro-2-methyl-2H-indazol-5-yl)imino]-3-[(1-methyl-1H-1,2,4-triazol-3-yl)methyl]-1-(2,4,5-trifluorobenzyl)-1,3,5-triazinane-2,4-dione (287.0 mg, yield: 75.3%, purity: 91.3%).

Example 7

A solution of 6-ethylthio-3-[(1-methyl-1H-1,2,4-triazol-3-yl)methyl]-1-(2,4,5-trifluorobenzyl)-1,3,5-triazine-2,4(1H,3H)-dione (300 mg, 0.727 mmol) and 6-chloro-2-methyl-2H-indazol-5-amine (172 mg, 0.946 mmol) in THF (6 mL) was firstly added dropwise with potassium tert-butoxide (1M in THF, 0.49 mL, 0.49 mmol) at 0° C., and the reaction mixture was stirred for 30 min and then added dropwise with potassium tert-butoxide (1M in THF, 0.97 mL, 0.97 mmol). The reaction mixture was stirred at 0° C. for 2.5 h, and then reacted at room temperature for 40 min. The reaction system was quenched with aqueous NH$_4$Cl solution, and the aqueous layer was extracted with EtOAc. The organic layer was washed with brine, dried over MgSO$_4$, and concentrated under reduced pressure to obtain a yellow solid (6E)-6-[(6-chloro-2-methyl-2H-indazol-5-yl)imino]-3-[(1-methyl-1H-1,2,4-triazol-3-yl)methyl]-1-(2,4,5-trifluorobenzyl)-1,3,5-triazinane-2,4-dione (292.4 mg, yield: 76.7%, purity: 90.4%).

Example 8

A solution of 6-ethylthio-3-[(1-methyl-1H-1,2,4-triazol-3-yl)methyl]-1-(2,4,5-trifluorobenzyl)-1,3,5-triazine-2,4(1H,3H)-dione (300 mg, 0.727 mmol) and 6-chloro-2-methyl-2H-indazol-5-amine (172 mg, 0.946 mmol) in THF (6 mL) was firstly added dropwise with LHMDS (1M in THF, 0.49 mL, 0.49 mmol) at 0° C., and the reaction mixture was stirred for 30 min and then added dropwise with LHMDS (1M in THF, 0.97 mL, 0.97 mmol). The reaction mixture was stirred at 0° C. for 2.5 h, then stirred at room temperature for 40 min, and added with 1.2 mL of N-methylpyrrolidone and stirred until the reaction was substantially completed. The reaction system was quenched with aqueous NH$_4$Cl solution, and the aqueous layer was extracted with EtOAc. The organic layer was washed with brine, dried over MgSO$_4$, and concentrated under reduced pressure to obtain a yellow solid (6E)-6-[(6-chloro-2-methyl-2H-indazol-5-yl)imino]-3-[(1-methyl-1H-1,2,4-triazol-3-yl)methyl]-1-(2,4,5-trifluorobenzyl)-1,3,5-triazinane-2,4-dione (304.6 mg, yield: 79.9%, purity: 93.1%).

Example 9

A solution of 6-ethylthio-3-[(1-methyl-1H-1,2,4-triazol-3-yl)methyl]-1-(2,4,5-trifluorobenzyl)-1,3,5-triazine-2,4(1H,3H)-dione (300 mg, 0.727 mmol) and 6-chloro-2-methyl-2H-indazol-5-amine (172 mg, 0.946 mmol) in THF (6 mL) was firstly added dropwise with LHMDS (1M in THF, 0.97 mL, 0.97 mmol) at 0° C., and the reaction mixture was stirred for 30 min and then added dropwise with LHMDS (1M in THF, 0.49 mL, 0.49 mmol). The reaction mixture was stirred at 0° C. for 2.5 h, and then reacted at room temperature for 40 min. The reaction system was quenched with aqueous NH$_4$Cl solution, and the aqueous layer was extracted with EtOAc. The organic layer was washed with brine, dried over MgSO$_4$, and concentrated under reduced pressure. The residue was purified by silica gel column chromatography (CHCl$_3$/MeOH gradient, 0-20% MeOH). The solid was solidized with acetone/H$_2$O (volume ratio: 1:1) to obtain a pale yellow solid (6E)-6-[(6-chloro-2-methyl-2H-indazol-5-yl)imino]-3-[(1-methyl-1H-1,2,4-triazol-3-yl)methyl]-1-(2,4,5-trifluorobenzyl)-1,3,5-triazinane-2,4-dione (244.0 mg, yield: 64.0%, purity: 96.5%).

Example 10

A solution of 6-ethylthio-3-[(1-methyl-1H-1,2,4-triazol-3-yl)methyl]-1-(2,4,5-trifluorobenzyl)-1,3,5-triazine-2,4(1H,3H)-dione (300 mg, 0.727 mmol) and 6-chloro-2-methyl-2H-indazol-5-amine (172 mg, 0.946 mmol) in THF (6 mL) was firstly added dropwise with LHMDS (1M in THF, 0.49 mL, 0.49 mmol) at 0° C., the reaction mixture was stirred for 30 min and then added dropwise with LHMDS (1M in THF, 0.49 mL, 0.49 mmol), and the reaction mixture was stirred for another 30 min and then added dropwise with LHMDS (1 M in THF, 0.49 mL, 0.49 mmol). The reaction mixture was stirred at 0° C. for 2.5 h, and then reacted at room temperature for 40 min. The reaction system was quenched with aqueous NH$_4$Cl solution, and the aqueous layer was extracted with EtOAc. The organic layer was washed with brine, dried over MgSO$_4$, and concentrated under reduced pressure. The residue was purified by silica gel column chromatography (CHCl$_3$/MeOH gradient, 0-20% MeOH). The solid was solidized with acetone/H$_2$O (volume ratio: 1:1) to obtain a pale yellow solid (6E)-6-[(6-chloro-2-methyl-2H-indazol-5-yl)imino]-3-[(1-methyl-1H-1,2,4-triazol-3-yl)methyl]-1-(2,4,5-trifluorobenzyl)-1,3,5-triazinane-2,4-dione (253.9 mg, yield: 66.6%, purity: 97.4%).

Example 11

To a solution of 6-ethylthio-3-[(1-methyl-1H-1,2,4-triazol-3-yl)methyl]-1-(2,4,5-trifluorobenzyl)-1,3,5-triazine-2,4(1H,3H)-dione (300 mg, 0.727 mmol) and 6-chloro-2-methyl-2H-indazol-5-amine (172 mg, 0.946 mmol) in THF (6 mL) was dropwise added LHMDS (1M in THF, 1.46 mL, 1.46 mmol) at 0° C. The reaction mixture was stirred at 0° C. for 2.5 h, then stirred at room temperature for 40 min, and added with 1.2 mL of isopropanol and stirred until the reaction was substantially completed. The reaction system was quenched with aqueous NH$_4$Cl solution, and the aqueous layer was extracted with EtOAc. The organic layer was washed with brine, dried over MgSO$_4$, and concentrated under reduced pressure. The residue was purified by silica gel column chromatography (CHCl$_3$/MeOH gradient, 0-20% MeOH). The solid was solidized with acetone/H$_2$O (volume ratio: 1:1) to obtain a pale yellow solid (6E)-6-[(6-chloro-2-methyl-2H-indazol-5-yl)imino]-3-[(1-methyl-1H-1,2,4-triazol-3-yl)methyl]-1-(2,4,5-trifluorobenzyl)-1,3,5-triazinane-2,4-dione (248.2 mg, yield: 65.1%, purity: 96.9%).

Example 12

To a solution of 6-ethylthio-3-[(1-methyl-1H-1,2,4-triazol-3-yl)methyl]-1-(2,4,5-trifluorobenzyl)-1,3,5-triazine-2,4(1H,3H)-dione (300 mg, 0.727 mmol) and 6-chloro-2-methyl-2H-indazol-5-amine (172 mg, 0.946 mmol) in THF (6 mL) was dropwise added LHMDS (1M in THF, 1.46 mL, 1.46 mmol) at 0° C. The reaction mixture was stirred at 0° C. for 2.5 h, then stirred at room temperature for 40 min, and added with 1.2 mL of acetone and stirred until the reaction was substantially completed. The reaction system was quenched with aqueous NH$_4$Cl solution, and the aqueous layer was extracted with EtOAc. The organic layer was washed with brine, dried over MgSO$_4$, and concentrated under reduced pressure. The residue was purified by silica gel column chromatography (CHCl$_3$/MeOH gradient, 0-20% MeOH). The solid was solidified with acetone/H$_2$O (volume ratio: 1:1) to obtain a pale yellow solid (6E)-6-[(6-chloro-2-methyl-2H-indazol-5-yl)imino]-3-[(1-methyl-1H-1,2,4-triazol-3-yl)methyl]-1-(2,4,5-trifluorobenzyl)-1,3,5-triazinane-2,4-dione (239.0 mg, yield: 62.7%, purity: 95.0%).

Example 13

To a solution of 6-ethylthio-3-[(1-methyl-1H-1,2,4-triazol-3-yl)methyl]-1-(2,4,5-trifluorobenzyl)-1,3,5-triazine-2,4(1H,3H)-dione (300 mg, 0.727 mmol) and 6-chloro-2-methyl-2H-indazol-5-amine (172 mg, 0.946 mmol) in THF (6 mL) was dropwise added LHMDS (1M in THF, 1.46 mL, 1.46 mmol) at 0° C. The reaction mixture was stirred at 0° C. for 2.5 h, then stirred at room temperature for 40 min, and added with 1.2 mL of isopropanol and stirred until the reaction was substantially completed. The reaction system was quenched with aqueous NH$_4$Cl solution, and the aqueous layer was extracted with EtOAc. The organic layer was washed with brine, dried over MgSO$_4$, and concentrated under reduced pressure. The residue was dispersed in 5 mL of isopropanol, and the mixture was stirred, heated to reflux, cooled and filtered by suction. The resulting filter cake was dried in vacuum to obtain a white solid powder (6E)-6-[(6-chloro-2-methyl-2H-indazol-5-yl)imino]-3-[(1-methyl-1H-1,2,4-triazol-3-yl)methyl]-1-(2,4,5-trifluorobenzyl)-1,3,5-triazinane-2,4-dione (258.1 mg, yield: 67.7%, purity: 98.5%).

Example 14

A solution of 6-ethylthio-3-[(1-methyl-1H-1,2,4-triazol-3-yl)methyl]-1-(2,4,5-trifluorobenzyl)-1,3,5-triazine-2,4(1H,3H)-dione (300 mg, 0.727 mmol) and 6-chloro-2-methyl-2H-indazol-5-amine (172 mg, 0.946 mmol) in THF (6 mL) was firstly added dropwise with LHMDS (1M in THF, 0.49 mL, 0.49 mmol) at 0° C., the reaction mixture was stirred for 30 min and then added dropwise with LHMDS (1M in THF, 0.49 mL, 0.49 mmol), and the reaction mixture was stirred for another 30 min and then added dropwise with LHMDS (1M in THF, 0.49 mL, 0.49 mmol). The reaction mixture was stirred at 0° C. for 2.5 h, and then reacted at room temperature for 40 min. The reaction system was quenched with aqueous NH$_4$Cl solution, and the aqueous layer was extracted with EtOAc. The organic layer was washed with brine, dried over MgSO$_4$, and concentrated under reduced pressure. The residue was recrystallized from dichloromethane/di-isopropyl ether (volume ratio: 5:1) and then dried in vacuum to obtain a pale pink solid. The pale pink solid was dispersed in 2 mL of isopropanol, and the mixture was stirred, heated to reflux, cooled and filtered by suction. The resulting filter cake was dried in vacuum to obtain a white solid powder (6E)-6-[(6-chloro-2-methyl-2H-indazol-5-yl)imino]-3-[(1-methyl-1H-1,2,4-triazol-3-yl)methyl]-1-(2,4,5-trifluorobenzyl)-1,3,5-triazinane-2,4-dione (254.6 mg, yield: 66.8%, purity: 99.5%).

Example 15

A solution of 6-ethylthio-3-[(1-methyl-1H-1,2,4-triazol-3-yl)methyl]-1-(2,4,5-trifluorobenzyl)-1,3,5-triazine-2,4(1H,3H)-dione (300 mg, 0.727 mmol) and 6-chloro-2-methyl-2H-indazol-5-amine (172 mg, 0.946 mmol) in THF (6 mL) was firstly added dropwise with LHMDS (1M in THF, 0.97 mL, 0.97 mmol) at 0° C., and the reaction mixture was stirred for 30 min and then added dropwise with LHMDS (1M in THF, 0.49 mL, 0.49 mmol). The reaction mixture was stirred at 0° C. for 2.5 h, and then reacted at room temperature for 40 min. The reaction system was quenched with aqueous NH$_4$Cl solution, and the aqueous layer was extracted with EtOAc. The organic layer was washed with brine, dried over MgSO$_4$, and concentrated under reduced pressure. The residue was recrystallized from dichloromethane/di-isopropyl ether (volume ratio: 5:1) and then dried in vacuum to obtain a pale pink solid. The pale pink solid was dispersed in 2 mL of isopropanol, and the mixture was stirred, heated to reflux, cooled and filtered by suction. The resulting filter cake was dried in vacuum to obtain a white solid powder (6E)-6-[(6-chloro-2-methyl-2H-indazol-5-yl)imino]-3-[(1-methyl-1H-1,2,4-triazol-3-yl)methyl]-1-(2,4,5-trifluorobenzyl)-1,3,5-triazinane-2,4-dione (252.7 mg, yield: 66.3%, purity: 99.4%).

Example 16

To a solution of 6-ethylthio-3-[(1-methyl-1H-1,2,4-triazol-3-yl)methyl]-1-(2,4,5-trifluorobenzyl)-1,3,5-triazine-2,4(1H,3H)-dione (300 mg, 0.727 mmol) and 6-chloro-2-methyl-2H-indazol-5-amine (172 mg, 0.946 mmol) in THF (6 mL) was dropwise added LHMDS (1M in THF, 1.46 mL, 1.46 mmol) at 0° C. The reaction mixture was stirred at 0° C. for 2.5 h, then stirred at room temperature for 40 min, and added with 1.2 mL of isopropanol and stirred until the reaction was substantially completed. The reaction system was quenched with aqueous NH$_4$Cl solution, and the aqueous layer was extracted with EtOAc. The organic layer was washed with brine, dried over MgSO$_4$, and concentrated under reduced pressure. The residue was recrystallized from dichloromethane/di-isopropyl ether (volume ratio: 5:1) and then dried in vacuum to obtain a pale pink solid. The pale pink solid was dispersed in 2 mL of isopropanol, and the mixture was stirred, heated to reflux, cooled and filtered by suction. The resulting filter cake was dried in vacuum to obtain a white solid powder (6E)-6-[(6-chloro-2-methyl-2H-indazol-5-yl)imino]-3-[(1-methyl-1H-1,2,4-triazol-3-yl)methyl]-1-(2,4,5-trifluorobenzyl)-1,3,5-triazinane-2,4-dione (248.2 mg, yield: 65.1%, purity: 99.2%).

Example 17

To a solution of 6-ethylthio-3-[(1-methyl-1H-1,2,4-triazol-3-yl)methyl]-1-(2,4,5-trifluorobenzyl)-1,3,5-triazine-2, 4(1H,3H)-dione (300 mg, 0.727 mmol) and 6-chloro-2-methyl-2H-indazol-5-amine (172 mg, 0.946 mmol) in THF (6 mL) was dropwise added LHMDS (1M in THF, 1.46 mL, 1.46 mmol) at 0° C. The reaction mixture was stirred at 0° C. for 2.5 h, then stirred at room temperature for 40 min, and added with 1.2 mL of acetone and stirred until the reaction was substantially completed. The reaction system was quenched with aqueous $NH_4Cl$ solution, and the aqueous layer was extracted with EtOAc. The organic layer was washed with brine, dried over $MgSO_4$, and concentrated under reduced pressure. The residue was recrystallized from dichloromethane/di-isopropyl ether (volume ratio: 5:1) and then dried in vacuum to obtain a pale pink solid. The pale pink solid was dispersed in 2 mL of isopropanol, and the mixture was stirred, heated to reflux, cooled and filtered by suction. The resulting filter cake was dried in vacuum to obtain a white solid powder (6E)-6-[(6-chloro-2-methyl-2H-indazol-5-yl)imino]-3-[(1-methyl-1H-1,2,4-triazol-3-yl)methyl]-1-(2,4,5-trifluorobenzyl)-1,3,5-triazinane-2,4-dione (251.2 mg, yield: 65.9%, purity: 99.3%).

Example 18

To a solution of 6-ethylthio-3-[(1-methyl-1H-1,2,4-triazol-3-yl)methyl]-1-(2,4,5-trifluorobenzyl)-1,3,5-triazine-2,4(1H,3H)-dione (300 mg, 0.727 mmol) and 6-chloro-2-methyl-2H-indazol-5-amine (172 mg, 0.946 mmol) in THF (6 mL) was dropwise added LHMDS (1M in THF, 1.46 mL, 1.46 mmol) at 0° C. The reaction mixture was stirred at 0° C. for 2.5 h, then stirred at room temperature for 40 min, and added with 1.2 mL of anhydrous acetonitrile and stirred until the reaction was substantially completed. The reaction system was quenched with aqueous $NH_4C_1$ solution, and the aqueous layer was extracted with EtOAc. The organic layer was washed with brine, dried over $MgSO_4$, and concentrated under reduced pressure. The residue was recrystallized from dichloromethane/di-isopropyl ether (volume ratio: 5:1) and then dried in vacuum to obtain a pale pink solid. The pale pink solid was dispersed in 2 mL of isopropanol, and the mixture was stirred, heated to reflux, cooled and filtered by suction. The resulting filter cake was dried under vacuum to obtain a white solid powder (6E)-6-[(6-chloro-2-methyl-2H-indazol-5-yl)imino]-3-[(1-methyl-1H-1,2,4-triazol-3-yl)methyl]-1-(2,4,5-trifluorobenzyl)-1,3,5-triazinane-2,4-dione (249.3 mg, yield: 65.4%, purity: 99.1%).

Example 19

To a solution of 6-ethylthio-3-[(1-methyl-1H-1,2,4-triazol-3-yl)methyl]-1-(2,4,5-trifluorobenzyl)-1,3,5-triazine-2,4(1H,3H)-dione (300 mg, 0.727 mmol) and 6-chloro-2-methyl-2H-indazol-5-amine (172 mg, 0.946 mmol) in THF (6 mL) was dropwise added LHMDS (1M in THF, 1.46 mL, 1.46 mmol) at 0° C. The reaction mixture was stirred at 0° C. for 2.5 h, and then reacted at room temperature for 40 min. The reaction system was quenched with aqueous $NH_4Cl$ solution, and the aqueous layer was extracted with EtOAc. The organic layer was washed with brine, dried over $MgSO_4$, and concentrated under reduced pressure. The residue was dispersed in 5 mL of isopropanol, and the mixture was stirred, heated to reflux, cooled and filtered by suction. The resulting filter cake was dried in vacuum to obtain a white solid powder (6E)-6-[(6-chloro-2-methyl-2H-indazol-5-yl)imino]-3-[(1-methyl-1H-1,2,4-triazol-3-yl)methyl]-1-(2,4,5-trifluorobenzyl)-1,3,5-triazinane-2,4-dione (125.8 mg, yield: 33.0%, purity: 95.1%).

Example 20

To a solution of 6-ethylthio-3-[(1-methyl-1H-1,2,4-triazol-3-yl)methyl]-1-(2,4,5-trifluorobenzyl)-1,3,5-triazine-2,4(1H,3H)-dione (300 mg, 0.727 mmol) and 6-chloro-2-methyl-2H-indazol-5-amine (172 mg, 0.946 mmol) in THF (6 mL) was dropwise added LHMDS (1M in THF, 1.46 mL, 1.46 mmol) at 0° C. The reaction mixture was stirred at 0° C. for 2.5 h, and then reacted at room temperature for 40 min. The reaction system was quenched with aqueous $NH_4Cl$ solution, and the aqueous layer was extracted with EtOAc. The organic layer was washed with brine, dried over $MgSO_4$, and concentrated under reduced pressure. The residue was dispersed in 5 mL of isopropanol; the mixture was stirred and heated to reflux; subsequently the mixture was added with 2 mL of di-isopropyl ether, stirred, heated to reflux, cooled and filtered by suction. The resulting filter cake was dried in vacuum to obtain a white solid powder (6E)-6-[(6-chloro-2-methyl-2H-indazol-5-yl)imino]-3-[(1-methyl-1H-1,2,4-triazol-3-yl)methyl]-1-(2,4,5-trifluorobenzyl)-1,3,5-triazinane-2,4-dione (127.3 mg, yield: 33.4%, purity: 95.3%).

Example 21

To a solution of 6-ethylthio-3-[(1-methyl-1H-1,2,4-triazol-3-yl)methyl]-1-(2,4,5-trifluorobenzyl)-1,3,5-triazine-2,4(1H,3H)-dione (300 mg, 0.727 mmol) and 6-chloro-2-methyl-2H-indazol-5-amine (172 mg, 0.946 mmol) in THF (6 mL) was dropwise added LHMDS (1M in THF, 1.46 mL, 1.46 mmol) at 0° C. The reaction mixture was stirred at 0° C. for 2.5 h, and then reacted at room temperature for 40 min. The reaction system was quenched with aqueous $NH_4Cl$ solution, and the aqueous layer was extracted with EtOAc. The organic layer was washed with brine, dried over $MgSO_4$, and concentrated under reduced pressure. The residue was solidized with acetone/$H_2O$ (volume ratio: 1:1); the resulting solid was dispersed in 2 mL of isopropanol, and the mixture was stirred, heated to reflux, cooled and filtered by suction. The resulting filter cake was dried in vacuum to obtain a white solid powder (6E)-6-[(6-chloro-2-methyl-2H-indazol-5-yl)imino]-3-[(1-methyl-1H-1,2,4-triazol-3-yl)methyl]-1-(2,4,5-trifluorobenzyl)-1,3,5-triazinane-2,4-dione (120.1 mg, yield: 31.5%, purity: 96.5%).

Example 22

To a solution of 6-ethylthio-3-[(1-methyl-1H-1,2,4-triazol-3-yl)methyl]-1-(2,4,5-trifluorobenzyl)-1,3,5-triazine-2,4(1H,3H)-dione (300 mg, 0.727 mmol) and 6-chloro-2-methyl-2H-indazol-5-amine (172 mg, 0.946 mmol) in THF (6 mL) was dropwise added LHMDS (1M in THF, 1.46 mL, 1.46 mmol) at 0° C. The reaction mixture was stirred at 0° C. for 2.5 h, and then reacted at room temperature for 40 min. The reaction system was quenched with aqueous $NH_4Cl$ solution, and the aqueous layer was extracted with EtOAc. The organic layer was washed with brine, dried over $MgSO_4$, and concentrated under reduced pressure. The residue was solidized with acetone/$H_2O$ (volume ratio: 1:1); the resulting solid was dispersed in 2 mL of isopropanol, and the mixture was stirred and heated to reflux; subsequently the mixture was added with 2 mL of di-isopropyl ether, stirred, heated to reflux, cooled and filtered by suction. The resulting filter cake was dried in vacuum to obtain a white solid powder (6E)-6-[(6-chloro-2-methyl-2H-indazol-5-yl)

imino]-3-[(1-methyl-1H-1,2,4-triazol-3-yl)methyl]-1-(2,4,5-trifluorobenzyl)-1,3,5-triazinane-2,4-dione (117.0 mg, yield: 30.7%, purity: 96.7%).

Example 23

To a solution of 6-ethylthio-3-[(1-methyl-1H-1,2,4-triazol-3-yl)methyl]-1-(2,4,5-trifluorobenzyl)-1,3,5-triazine-2,4(1H,3H)-dione (300 mg, 0.727 mmol) and 6-chloro-2-methyl-2H-indazol-5-amine (172 mg, 0.946 mmol) in THF (6 mL) was dropwise added LHMDS (1M in THF, 1.46 mL, 1.46 mmol) at 0° C. The reaction mixture was stirred at 0° C. for 2.5 h, and then reacted at room temperature for 40 min. The reaction system was quenched with aqueous $NH_4Cl$ solution, and the aqueous layer was extracted with EtOAc. The organic layer was washed with brine, dried over $MgSO_4$, and concentrated under reduced pressure. The residue was recrystallized from dichloromethane/di-isopropyl ether (volume ratio: 5:1) and then dried in vacuum to obtain a pale pink solid. The pale pink solid was dispersed in 2 mL of isopropanol, and the mixture was stirred, heated to reflux, cooled and filtered by suction. The resulting filter cake was dried in vacuum to obtain a white solid powder (6E)-6-[(6-chloro-2-methyl-2H-indazol-5-yl)imino]-3-[(1-methyl-1H-1,2,4-triazol-3-yl)methyl]-1-(2,4,5-trifluorobenzyl)-1,3,5-triazinane-2,4-dione (118.6 mg, yield: 31.1%, purity: 97.2%).

Example 24

To a solution of 6-ethylthio-3-[(1-methyl-1H-1,2,4-triazol-3-yl)methyl]-1-(2,4,5-trifluorobenzyl)-1,3,5-triazine-2,4(1H,3H)-dione (300 mg, 0.727 mmol) and 6-chloro-2-methyl-2H-indazol-5-amine (172 mg, 0.946 mmol) in THF (6 mL) was dropwise added LHMDS (1M in THF, 1.46 mL, 1.46 mmol) at 0° C. The reaction mixture was stirred at 0° C. for 2.5 h, and then reacted at room temperature for 40 min. The reaction system was quenched with aqueous $NH_4Cl$ solution, and the aqueous layer was extracted with EtOAc. The organic layer was washed with brine, dried over $MgSO_4$, and concentrated under reduced pressure. The residue was recrystallized from acetic acid/di-isopropyl ether (volume ratio: 2:1) and then dried in vacuum to obtain a pale pink solid. The pale pink solid was dispersed in 2 mL of isopropanol, and the mixture was stirred, heated to reflux, cooled and filtered by suction. The resulting filter cake was dried in vacuum to obtain a white solid powder (6E)-6-[(6-chloro-2-methyl-2H-indazol-5-yl)imino]-3-[(1-methyl-1H-1,2,4-triazol-3-yl)methyl]-1-(2,4,5-trifluorobenzyl)-1,3,5-triazinane-2,4-dione (119.3 mg, yield: 31.3%, purity: 97.9%).

Example 25

To a solution of 6-ethylthio-3-[(1-methyl-1H-1,2,4-triazol-3-yl)methyl]-1-(2,4,5-trifluorobenzyl)-1,3,5-triazine-2,4(1H,3H)-dione (300 mg, 0.727 mmol) and 6-chloro-2-methyl-2H-indazol-5-amine (172 mg, 0.946 mmol) in THF (6 mL) was dropwise added LHMDS (1M in THF, 1.46 mL, 1.46 mmol) at 0° C. The reaction mixture was stirred at 0° C. for 2.5 h, and then reacted at room temperature for 40 min. The reaction system was quenched with aqueous $NH_4Cl$ solution, and the aqueous layer was extracted with EtOAc. The organic layer was washed with brine, dried over $MgSO_4$, and concentrated under reduced pressure. The residue was recrystallized from acetic acid/di-isopropyl ether (volume ratio: 2:1) and then dried in vacuum to obtain a pale pink solid. The pale pink solid was dispersed in 2 mL of isopropanol, and the mixture was stirred, heated to reflux, cooled and filtered by suction. The resulting filter cake was recrystallized again from acetic acid/di-isopropyl ether (volume ratio: 2:1) and then dried in vacuum to obtain a white solid. The white solid was dispersed in 2 mL of acetone, and the mixture was stirred, heated to reflux, cooled and filtered by suction. The resulting filter cake was dried in vacuum to obtain a white solid powder (6E)-6-[(6-chloro-2-methyl-2H-indazol-5-yl)imino]-3-[(1-methyl-1H-1,2,4-triazol-3-yl)methyl]-1-(2,4,5-trifluorobenzyl)-1,3,5-triazinane-2,4-dione (115.5 mg, yield: 30.3%, purity: 97.9%).

Example 26

A solution of 6-ethylthio-3-[(1-methyl-1H-1,2,4-triazol-3-yl)methyl]-1-(2,4,5-trifluorobenzyl)-1,3,5-triazine-2,4(1H,3H)-dione (300 mg, 0.727 mmol) and 6-chloro-2-methyl-2H-indazol-5-amine (172 mg, 0.946 mmol) in THF (6 mL) was firstly added dropwise with LHMDS (1M in THF, 0.97 mL, 0.97 mmol) at 0° C., and the mixture was stirred for 30 min and then added dropwise with LHMDS (1 M in THF, 0.49 mL, 0.49 mmol). The reaction mixture was stirred at 0° C. for 2.5 h, and then reacted at room temperature for 40 min. The reaction system was quenched with aqueous $NH_4Cl$ solution, and the aqueous layer was extracted with EtOAc. The organic layer was washed with brine, dried over $MgSO_4$, and concentrated under reduced pressure. The residue was dispersed in 5 mL of isopropanol, and the mixture was stirred, heated to reflux, cooled and filtered by suction. The resulting filter cake was dried in vacuum to obtain a white solid powder (6E)-6-[(6-chloro-2-methyl-2H-indazol-5-yl)imino]-3-[(1-methyl-1H-1,2,4-triazol-3-yl)methyl]-1-(2,4,5-trifluorobenzyl)-1,3,5-triazinane-2,4-dione (262.6 mg, yield: 68.9%, purity: 98.8%).

Example 27

The purity of the products of the above Comparative Examples 1-2 and Examples 1-26 was determined by HPLC analysis, i.e., by calculating the percentage of the peak area of the target compound to the peak areas of all peaks. The respective content (i.e., purity) and retention time of compound 1 (i.e., (6E)-6-[(6-chloro-2-methyl-2H-indazol-5-yl)imino]-3-[(1-methyl-1H-1,2,4-triazol-3-yl)methyl]-1-(2,4,5-trifluorobenzyl)-1,3,5-triazinane-2,4-dione) and the impurity compound A in the representative Comparative Examples 1-2 and Examples 3, 8, 10, 13 and 14 are shown in the following table.

| Examples | Content of compound 1 | Retention time (min) | Content of compound A | Retention time (min) |
| --- | --- | --- | --- | --- |
| Comparative Example 1 | 80.1% | 18.7 | 0.119% | 21.3 |
| Comparative Example 2 | 86.2% | 18.7 | 0.119% | 21.3 |
| Example 3 | 91.9% | 18.7 | 0 | — |
| Example 8 | 93.1% | 18.7 | 0 | — |
| Example 10 | 97.4% | 18.7 | 0 | — |
| Example 13 | 98.5% | 18.7 | 0 | — |
| Example 14 | 99.5% | 18.7 | 0 | — |

It could be seen from analysis of the HPLC results of the above examples that the peak at a retention time of 18.7 min corresponded to compound 1; the peak at a retention time of 21.3 min in Comparative Examples 1-2 corresponded to the impurity compound A. In contrast, the present invention can not only effectively increase the purity of compound 1, but also unexpectedly reduce or remove the impurity compound A with similar structure and polarity to compound 1, thereby obtaining compound 1 without the impurity compound A or with a relatively lower content of the impurity compound A through process improvement.

Example 28

A mixture of (6E)-6-[(6-chloro-2-methyl-2H-indazol-5-yl)imino]-3-[(1-methyl-1H-1,2,4-triazol-3-yl)methyl]-1-(2,4,5-trifluorobenzyl)-1,3,5-triazinane-2,4-dione (585 mg, 1.1 mmol, purity: 98.5%) prepared in Example 13 and fumaric acid (139 mg, 1.2 mmol) in EtOAc (3.0 mL) was stirred at room temperature for 45 min. The suspension was filtered to obtain a white solid (6E)-6-[(6-chloro-2-methyl-2H-indazol-5-yl)imino]-3-[(1-methyl-1H-1,2,4-triazol-3-yl)methyl]-1-(2,4,5-trifluorobenzyl)-1,3,5-triazinane-2,4-dione fumarate salt (705.9 mg, yield: 97.9%, purity: 99.8%, single impurity content of <0.1%).

Example 29

In accordance with the same method as in Example 28, (6E)-6-[(6-chloro-2-methyl-2H-indazol-5-yl)imino]-3-[(1-methyl-1H-1,2,4-triazol-3-yl)methyl]-1-(2,4,5-trifluorobenzyl)-1,3,5-triazinane-2,4-dione (585 mg, 1.1 mmol, purity: 96.7%) repeatedly prepared in Example 22 was used to prepare and obtain fumarate salt thereof as a solid form (672.0 mg, yield: 93.2%, purity: 99.3%).

Comparative Example 3

In accordance with the same method as in Example 28, (6E)-6-[(6-chloro-2-methyl-2H-indazol-5-yl)imino]-3-[(1-methyl-1H-1,2,4-triazol-3-yl)methyl]-1-(2,4,5-trifluorobenzyl)-1,3,5-triazinane-2,4-dione (585 mg, 1.1 mmol, purity: 86.2%) repeatedly prepared in Comparative Example 2 was used to prepare and obtain fumarate salt thereof as a solid form (612.9 mg, yield: 85.0%, purity: 92.4%).

Example 30

The performance of the drug powder is influenced by various factors, among which the fluidity, anti-caking property and the like of the starting material drug (i.e., active pharmaceutical ingredient) play a key role in the formulation design, the quality control, the process design, the industrial production and the like of the drug. In the pharmaceutical field, poor fluidity mainly affects the uniformity of the mixed material, and such mixed material is easy to delaminate and has uneven material content; at the same time, the resulting tablet are easy to delaminate during tableting, resulting in inconsistent content of the tablet pressed at different times, and it is easy to cause a significant difference in tablet weight.

The fluidity, the anti-caking property and the like of compound 1 (i.e., (6E)-6-[(6-chloro-2-methyl-2H-indazol-5-yl)imino]-3-[(1-methyl-1H-1,2,4-triazol-3-yl)methyl]-1-(2,4,5-trifluorobenzyl)-1,3,5-triazinane-2,4-dione with different purities) in the above Comparative Examples 1-2 and Examples 1-12 were measured by an intelligent powder comprehensive characteristic tester (HMKTest LABULK, model: HMKFlow 6393 PT1000).

The Carr index reflects the quality of the fluidity, and a smaller value indicates better fluidity, while a Carr index of more than 23% generally indicates poor fluidity. For anti-caking property, "good" means substantially no agglomeration or clumping, "less good" means partial clumping or agglomeration, and "poor" means severe or complete clumping. For fluidity, "good" means good solid state and good fluidity, which is favorable for formulation development; "less good" means average fluidity; and "poor" means poor fluidity, which cannot be used for formulation development.

| Examples | Parameters related to the solid form of compound 1 | | | |
|---|---|---|---|---|
| | Purity (%) | Carr index (%) | Anti-caking property | Fluidity |
| Example 1 | 90.2 | 21.4 | Less good | Good |
| Example 2 | 90.6 | 20.7 | Less good | Good |
| Example 3 | 91.9 | 18.7 | Less good | Good |
| Example 4 | 92.8 | 19.4 | Less good | Good |
| Example 5 | 92.5 | 18.8 | Less good | Good |
| Example 6 | 91.3 | 18.5 | Less good | Good |
| Example 7 | 90.4 | 17.1 | Less good | Good |
| Example 8 | 93.1 | 21.2 | Less good | Good |
| Example 9 | 96.5 | 12.6 | Good | Good |
| Example 10 | 97.4 | 13.4 | Good | Good |
| Example 11 | 96.9 | 14.1 | Good | Good |
| Example 12 | 95.0 | 15.1 | Good | Good |
| Comparative Example 1 | 80.1 | 42.1 | Poor | Poor |
| Comparative Example 2 | 86.2 | 39.4 | Poor | Poor |

Since compound 1 prepared in Comparative Examples 1-2 had a purity of below 90.0%, the resulting solid form of compound 1 had poor Carr index, anti-caking property and fluidity, and thus failed to meet the formulation requirements. Unexpectedly, compound 1 prepared in Examples 1-12 had a purity of 90.0% or higher, even 95.0% or higher, and the resulting solid form of compound 1 with a purity of 90.0% or higher had good fluidity and improved anti-caking property, and thus can meet the requirements of preparation development.

Similarly, the fluidity of the fumarate salt solid form of compound 1 prepared in the above Examples 28-29 and Comparative Example 3 was measured.

| Examples | Parameters related to the fumarate salt solid form of compound 1 | | |
|---|---|---|---|
| | Carr index (%) | Anti-caking property | Fluidity |
| Example 28 | 11.3 | Good | Good |
| Example 29 | 12.1 | Less good | Good |
| Comparative Example 3 | 36.1 | Poor | Poor |

The inventors of the present invention further find that salt-forming reaction of compound 1 having a purity of below 90% with an acid (e.g., fumaric acid) can obtain the fumarate salt of compound 1 having a purity of up to 92.4% (as in Comparative Example 3) and a Carr index of 36.1% that is still greater than 23%, so the resulting fumarate salt solid form is poor in anti-caking property and fluidity; unexpectedly, salt-forming reaction of compound 1 having a purity of 90% or higher and even 95% or higher with fumaric acid can obtain the fumarate salt of compound 1 having a purity of 99.8% and single impurity content of <0.1%, and moreover, the resulting fumarate salt solid form has a Carr index as low as 11-12%, and good anti-caking property and fluidity, and thus meets the formulation requirements.

Therefore, compound 1 having a purity of 90% or higher, even 95% or higher not only has better anti-caking property and fluidity, but also achieves unexpected technical effects in terms of the use of preparing an addition salt formed by compound 1 and an acid (such as fumaric acid), such as the prepared fumarate salt solid form of compound 1 with good fluidity, good anti-caking property, and high purity.

The specific examples described above further describe the purpose, technical schemes and beneficial effects of the present invention in detail. It should be understood that the above-mentioned specific examples are only examples of the present invention and should not be construed as limiting the protection scope of the present invention, and any modifications, equivalent replacements, improvements and the like made within the spirit and aim of the present invention should be included in the protection scope of the present invention.

What is claimed is:

1. A composition, comprising a compound of formula (I), in which the compound of formula (I) has a HPLC purity of ≥95%;

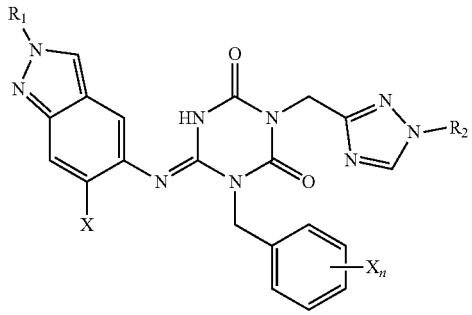

formula (I)

wherein $R_1$ and $R_2$ are each independently $C_1$-$C_6$ alkyl;

X is halogen;

n is an integer from 1 to 5, and a compound (6E)-6-[(6-chloro-1-methyl-1H-indazol-5-yl)imino]-3-[(1-methyl-1H-1,2,4-triazol-3-yl)methyl]-1-(2,4,5-trifluorobenzyl)-1,3,5-triazinane-2,4-dione, as an impurity in the composition, has a content of <0.1%.

2. The composition according to claim 1, in which the composition does not comprise the compound (6E)-6-[(6-chloro-1-methyl-1H-indazol-5-yl)imino]-3-[(1-methyl-1H-1,2,4-triazol-3-yl)methyl]-1-(2,4,5-trifluorobenzyl)-1,3,5-triazinane-2,4-dione.

3. The composition according to claim 1, in which the compound of formula (I) is

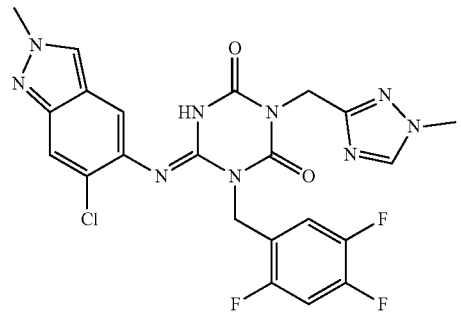

4. The composition according to claim 1, in which the composition is obtained from a method for purifying, and the method for purifying comprises the following steps:

(ii) dispersing the compound of formula (I) to be purified in one or more solvents, optionally heating, stirring and/or cooling, followed by filtrating to obtain the composition comprising the compound of formula (I).

5. The composition according to claim 4, in which the method for purifying comprises the following steps:

(i-a) recrystallizing a to-be-purified composition comprising the compound of formula (I) in a mixed solvent; and (ii-a) dispersing solid obtained in the step (i-a) in one or more solvents, optionally heating, stirring and/or cooling, followed by filtrating to obtain the composition comprising the compound of formula (I);

or (ii-b) dispersing the compound of formula (I) to be purified in one or more solvents, optionally heating, stirring and/or cooling, followed by filtrating to obtain a solid; and (i-b) recrystallizing the solid obtained in the step (ii-b) in a mixed solvent.

6. The composition according to claim 4, in which in the step (ii), the heating is performed at a temperature in the range of 40-80° C.;

in the step (ii), the cooling is performed at a temperature in the range of 0-35° C.;

and/or, in the step (ii), the solvent is water, $C_1$-$C_6$ alkyl alcohol, di-$C_1$-$C_6$ alkyl ether and/or $C_1$-$C_6$ alkyl ketone.

7. The composition according to claim 5, in which the step (i-a) or (i-b) further comprises filtering the solid obtained from recrystallization; and/or, the step (i-a) or (i-b) and/or the step (ii-a) or (ii-b) further comprises drying the solid.

8. The composition according to claim 5, in which in the step (i-a) or (i-b), the mixed solvent is a mixture of any two of $C_1$-$C_6$ halogenated alkane, $C_1$-$C_6$ alkyl carboxylic acid and di-$C_1$-$C_6$ alkyl ether.

9. The composition according to claim 4, in which the composition is a white solid.

10. The composition according to claim 1, in which the composition is obtained from a method for preparing, and the method for preparing comprises the following steps:
(a) reacting a compound of formula (II)

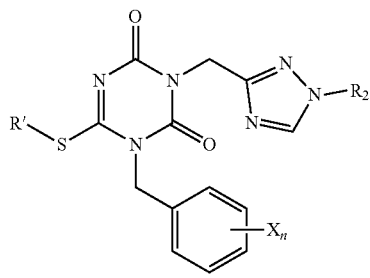

formula (II)

wherein,
R' is $C_1$-$C_6$ alkyl;
$R_2$, X and n are as defined in formula (I);
with a compound of formula (III)

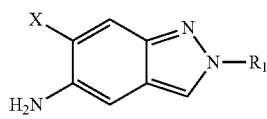

formula III wherein,
$R_1$ and X are as defined in formula (I);
in the presence of a base added in portions and/or a co-solvent to obtain the composition comprising the compound of the formula (I).

11. The composition according to claim 10, in which the compound of formula (II) is synthesized by the following steps:
(b) reacting a compound of formula (IV)

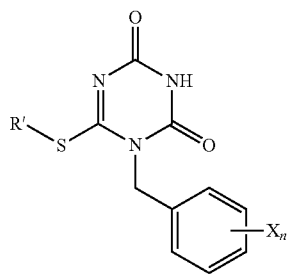

formula IV wherein,
R', X and n are as defined in formula (II);
with a compound of formula (V) or a salt thereof

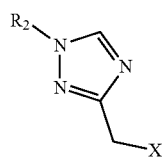

formula (V)

wherein,
$R_2$ and X are as defined in formula (II);
to obtain the compound of formula (II).

12. The composition according to claim 10, in which the co-solvent is selected from the group consisting of dioxane, $C_1$-$C_6$ alkyl ketone, $C_1$-$C_6$ alkyl alcohol, dimethylacetamide, dimethylformamide, acetonitrile, dimethylsulfoxide, N-methylpyrrolidone, and any mixture thereof.

13. The composition according to claim 10, in which the base added in portions is the base added in two or more portions.

14. The composition according to claim 10, in which the method for preparing further comprises a purification step.

15. The composition according to claim 14, in which the purification step is a column chromatography and/or recrystallization step.

16. The composition according to claim 10, in which X is fluorine or chlorine; and/or, n is an integer from 2 to 4.

17. A composition, comprising a physiologically acceptable salt of a compound of formula (I), in which the physiologically acceptable salt of the compound of formula (I) has a HPLC purity of ≥99%;

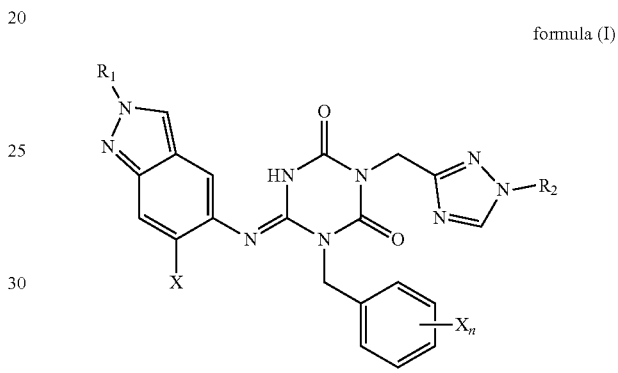

formula (I)

wherein
$R_1$ and $R_2$ are each independently $C_1$-$C_6$ alkyl;
X is halogen;
n is an integer from 1 to 5, and
a compound (6E)-6-[(6-chloro-1-methyl-1H-indazol-5-yl)imino]-3-[(1-methyl-1H-1,2,4-triazol-3-yl)methyl]-1-(2,4,5-trifluorobenzyl)-1,3,5-triazinane-2,4-dione, as an impurity in the composition, has a content of <0.1%, wherein the physiologically acceptable salt of the compound of formula (I) is a fumarate salt.

18. The composition according to claim 17, wherein the composition does not comprise the compound (6E)-6-[(6-chloro-1-methyl-1H-indazol-5-yl)imino]-3-[(1-methyl-1H-1,2,4-triazol-3-yl)methyl]-1-(2,4,5-trifluorobenzyl)-1,3,5-triazinane-2,4-dione.

19. The composition according to claim 17, wherein the compound of formula (I) is

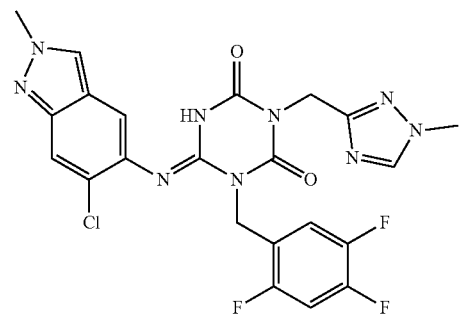

* * * * *

(12) EX PARTE REEXAMINATION CERTIFICATE (12999th)
United States Patent
Wei et al.

(10) Number: US 11,840,526 C1
(45) Certificate Issued: Jul. 29, 2025

(54) COMPOUNDS AND METHOD FOR PREPARING THE SAME

(71) Applicants: BEIJING GRAND JOHAMU PHARMACEUTICAL COMPANY, LTD., Beijing (CN); NANJING GRITPHARMACO., LTD., NanJing (CN)

(72) Inventors: Weiye Wei, Beijing (CN); Jiannan Yang, Beijing (CN); Xiaotao Wu, Beijing (CN); Taotao Zhao, Beijing (CN); Hao Wang, Beijing (CN); Chao Li, Beijing (CN); Lei Qu, Beijing (CN); Bin Wang, Beijing (CN)

(73) Assignees: BEIJING GRAND JOHAMU PHARMACEUTICAL COMPANY, LTD., Beijing (CN); NANJING GRITPHARMACO., LTD., Nanjing (CN)

Reexamination Request:
No. 90/019,517, May 22, 2024

Reexamination Certificate for:
Patent No.: 11,840,526
Issued: Dec. 12, 2023
Appl. No.: 17/900,071
Filed: Aug. 31, 2022

(30) Foreign Application Priority Data

May 10, 2022 (CN) .......................... 202210500289.8
May 10, 2022 (CN) .......................... 202210500291.5

(51) Int. Cl.
*A61K 31/427* (2006.01)
*A61P 31/14* (2006.01)
*C07D 403/14* (2006.01)

(52) U.S. Cl.
CPC .......... *C07D 403/14* (2013.01); *A61K 31/427* (2013.01); *A61P 31/14* (2018.01)

(58) Field of Classification Search
None
See application file for complete search history.

(56) References Cited

To view the complete listing of prior art documents cited during the proceeding for Reexamination Control Number 90/019,517, please refer to the USPTO's Patent Electronic System.

*Primary Examiner* — Joseph R Kosack

(57) ABSTRACT

The present invention provides a composition comprising a compound of formula (I) or a physiologically acceptable salt thereof, in which the compound of formula (I) or a physiologically acceptable salt thereof has a HPLC purity of ≥90%;

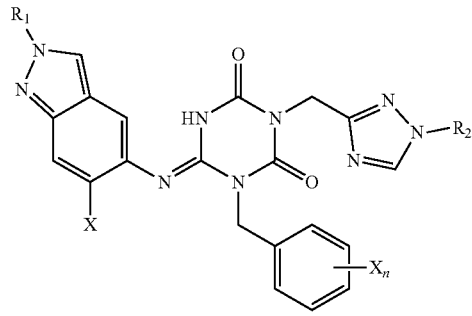

formula (I)

wherein $R_1$, $R_2$, X and n are as defined herein. The present invention further provides use of the composition according to the present invention for preparing and/or purifying a composition comprising a salt of the compound of formula (I), and a method for treating a disease caused by a coronavirus which comprises administering the composition of the present invention to a subject. The composition of the present invention comprises the compound of formula (I) with high purity, and has good fluidity and anti-caking property; moreover, the claimed composition comprising the compound of formula (I)) with high purity is more suitable for preparing a composition comprising a salt of the compound of formula (I) with higher purity.

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 9 is cancelled.

Claims 1 and 17 are determined to be patentable as amended.

Claims 2-8, 10-16, 18 and 19, dependent on an amended claim, are determined to be patentable.

New claims 20-60 are added and determined to be patentable.

1. A composition, comprising a compound of formula (I), in which the compound of formula (I) has a HPLC purity of ≥95%;

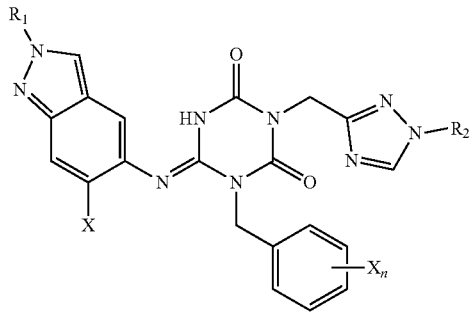

formula (I)

wherein $R_1$ and $R_2$ are each independently $C_1$-$C_6$ alkyl;

X is halogen;

n is an integer from 1 to 5, and a compound (6E)-6-[(6-chloro-1-methyl-1H-indazol-5-yl) imino]-3-[(1-methyl-1H-1,2,4-triazol-3-yl) methyl]-1-(2,4,5-trifluorobenzyl)-1,3,5-triazinane-2,4-dione, as an impurity in the composition, has a content of <0.1%, *wherein the physiologically acceptable salt of the compound of formula (I) is a fumarate salt.*

*20. A composition comprising a compound of formula (I), in which the compound of formula (I) has a HPLC purity of ≥95%;*

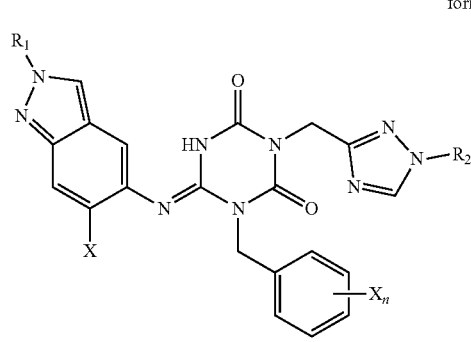

formula (I)

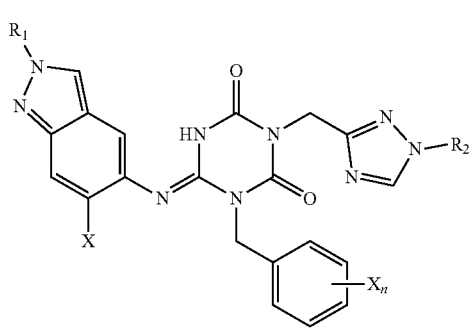

formula (I)

*wherein*

*$R_1$ and $R_2$ are each independently $C_1$-$C_6$ alkyl;*

X is halogen;

n is an integer from 1 to 5, and a compound (6E)-6-[(6-chloro-1-methyl-1H-indazol-5-yl)imino]-3-[(1-methyl-1H-1,2,4-triazol-3-yl)methyl]-1-(2,4,5-trifluorobenzyl)-1,3,5-triazinane-2,4-dione, as an impurity in the composition, has a content of <0.1%, *said composition being a white solid.*

17. A composition, comprising a physiologically acceptable salt of a compound of formula (I), in which the physiologically acceptable salt of the compound of formula (I) *is a white solid and* has a HPLC purity of ≥99%;

*wherein*

*$R_1$ and $R_2$ are each independently $C_1$-$C_6$ alkyl;*

*X is halogen;*

*n is an integer from 1 to 5, and*

*a compound (6E)-6-[(6-chloro-1-methyl-1H-indazol-5-yl) imino]-3-[(1-methyl-1H-1,2,4-triazol-3-yl) methyl]-1-(2,4,5-trifluorobenzyl)-1,3,5-triazinane-2,4-dione, as an impurity in the composition, has a content of <0.1%, said composition having a Carr index ranging from 12.6% to 15.1%.*

*21. The composition according to claim 20, in which the composition does not comprise the compound (6E)-6-[(6-chloro-1-methyl-1H-indazol-5-yl)imino]-3-[(1-methyl-1H-1,2,4-triazol-3-yl) methyl]-1-(2,4,5-trifluorobenzyl)-1,3,5-triazinane-2,4-dione.*

*22. The composition according to claim 20, in which the compound of formula (I) is*

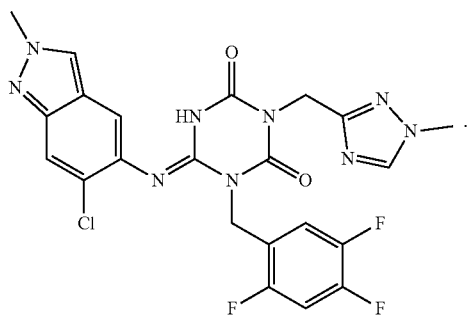

23. The composition according to claim 20, in which the composition is obtained from a method for purifying, and the method for purifying comprises the following steps:

(ii) dispersing the compound of formula (I) to be purified in one or more solvents, optionally heating, stirring and/or cooling, followed by filtrating to obtain the composition comprising the compound of formula (I).

24. The composition according to claim 23, in which the method for purifying comprises the following steps:

(i-a) recrystallizing a to-be-purified composition comprising the compound of formula (I) in a mixed solvent; and (ii-a) dispersing solid obtained in the step (i-a) in one or more solvents, optionally heating, stirring and/or cooling, followed by filtrating to obtain the composition comprising the compound of formula (I);

or (ii-b) dispersing the compound of formula (I) to be purified in one or more solvents, optionally heating, stirring and/or cooling, followed by filtrating to obtain a solid; and (i-b) recrystallizing the solid obtained in the step (ii-b) in a mixed solvent.

25. The composition according to claim 23, in which in the step (ii), the heating is performed at a temperature in the range of 40-80° C.;

in the step (ii), the cooling is performed at a temperature in the range of 0-35° C.; and/or, in the step (ii), the solvent is water, $C_1$-$C_6$ alkyl alcohol, di-$C_1$-$C_6$ alkyl ether and/or $C_1$-$C_6$ alkyl ketone.

26. The composition according to claim 24, in which the step (i-a) or (i-b) further comprises filtering the solid obtained from recrystallization; and/or, the step (i-a) or (i-b) and/or the step (ii-a) or (ii-b) further comprises drying the solid.

27. The composition according to claim 24, in which in the step (i-a) or (i-b), the mixed solvent is a mixture of any two of $C_1$-$C_6$ halogenated alkane, $C_1$-$C_6$ alkyl carboxylic acid and di-$C_1$-$C_6$ alkyl ether.

28. The composition according to claim 23, in which the composition is a white solid.

29. The composition according to claim 20, in which the composition is obtained from a method for preparing, and the method for preparing comprises the following steps:

(a) reacting a compound of formula (II)

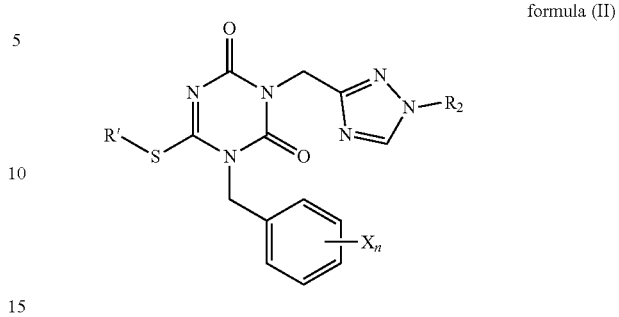

wherein,

R' is $C_1$-$C_6$ alkyl;

$R_2$, X and n are as defined in formula (I);

with a compound of formula (III)

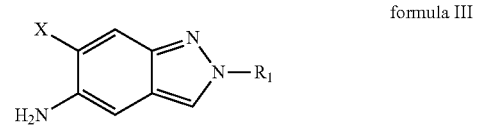

wherein, $R_1$ and X are as defined in formula (I);

in the presence of a base added in portions and/or a co-solvent to obtain the composition comprising the compound of the formula (I).

30. The composition according to claim 29 in which the compound of formula (II) is synthesized by the following steps:

(b) reacting a compound of formula (IV)

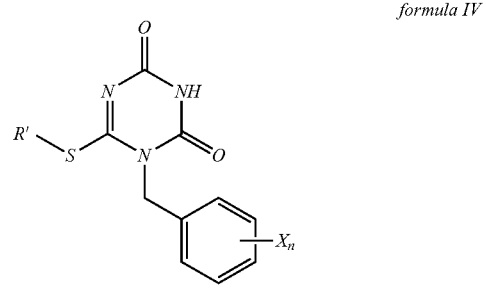

wherein,

R', X and n are as defined in formula (II);

with a compound of formula (V) or a salt thereof

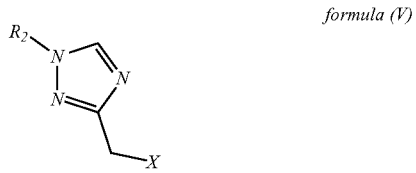

wherein, $R_2$ and X are as defined in formula (II);

to obtain the compound of formula (II).

31. The composition according to claim 29, in which the co-solvent is selected from the group consisting of dioxane, $C_1$-$C_6$ alkyl ketone, $C_1$-$C_6$ alkyl alcohol, dimethylacetamide, dimethylformamide, acetonitrile, dimethylsulfoxide, N-methylpyrrolidone, and any mixture thereof.

32. The composition according to claim 29, in which the base added in portions is the base added in two or more portions.

33. The composition according to claim 29, in which the method for preparing further comprises a purification step.

34. The composition according to claim 33, in which the purification step is a column chromatography and/or recrystallization step.

35. The composition according to claim 29, in which X is fluorine or chlorine; and/or, n is an integer from 2 to 4.

36. A composition, comprising a physiologically acceptable salt of a compound of formula (I), in which the physiologically acceptable salt of the compound of formula (I) has a HPLC purity of ≥99%;

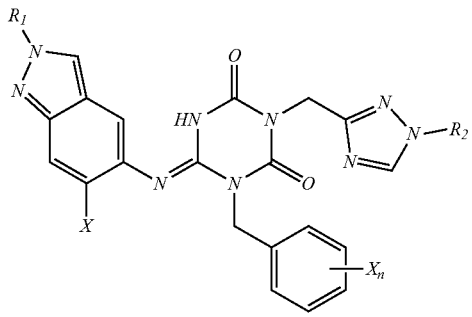

formula (I)

wherein
$R_1$ and $R_2$ are each independently $C_1$-$C_6$ alkyl;
X is halogen;
n is an integer from 1 to 5, and
a compound (6E)-6-[(6-chloro-1-methyl-1H-indazol-5-yl)iminol]-3-[(1-methyl-1H-1,2,4-triazol-3-yl) methyl]-1-(2,4,5-trifluorobenzyl)-1,3,5-triazinane-2,4-dione, as an impurity in the composition, has a content of <0.1%, wherein the physiologically acceptable salt of the compound of formula (I) is a fumarate salt, said composition having a Carr index ranging from 11.3% to 12.1%.

37. The composition according to claim 36, wherein the composition does not comprise the compound (6E)-6-[(6-chloro-1-methyl-1H-indazol-5-yl)imino]-3-[(1-methyl-1H-1,2,4-triazol-3-yl) methyl]-1-(2,4,5-trifluorobenzyl)-1,3,5-triazinane-2,4-dione.

38. The composition according to claim 36, wherein the compound of formula (I) is

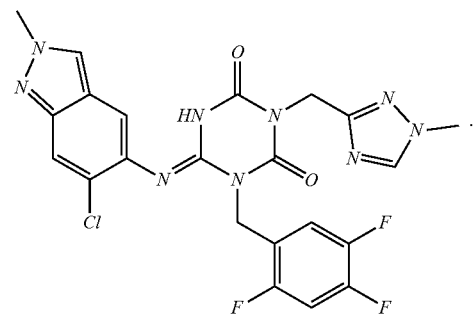

39. A composition, comprising a physiologically acceptable salt of a compound of formula (I), in which the physiologically acceptable salt of the compound of formula (I) has a HPLC purity of ≥99% and a Carr index ranging from 11.3% to 12.1%;

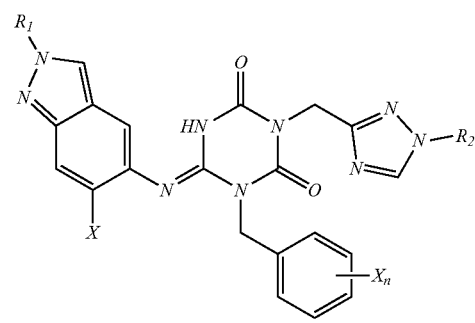

formula (I)

wherein
$R_1$ and $R_2$ are each independently $C_1$-$C_6$ alkyl;
X is halogen;
n is an integer from 1 to 5, and
a compound (6E)-6-[(6-chloro-1-methyl-1H-indazol-5-yl)imino]-3-[(1-methyl-1H-1,2,4-triazol-3-yl) methyl]-1-(2,4,5-trifluorobenzyl)-1,3,5-triazinane-2,4-dione, as an impurity in the composition, has a content of <0.1%, wherein the physiologically acceptable salt of the compound of formula (I) is a fumarate salt.

40. The composition according to claim 39, wherein the composition does not comprise the compound (6E)-6-[(6-chloro-1-methyl-1H-indazol-5-yl)imino]-3-[(1-methyl-1H-1,2,4-triazol-3-yl) methyl]-1-(2,4,5-trifluorobenzyl)-1,3,5-triazinane-2,4-dione.

41. The composition according to claim 39, wherein the compound of formula (I) is

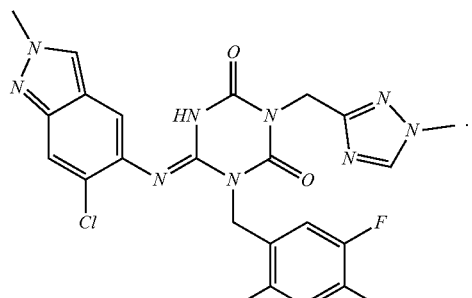

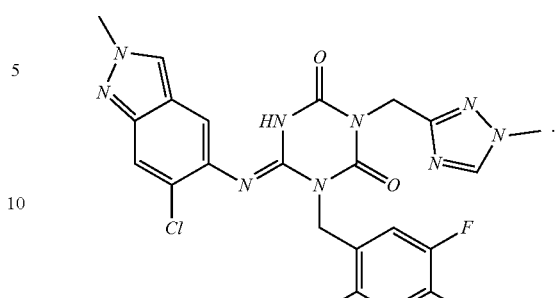

42. A composition comprising a compound of formula (I), in which the compound of formula (I) has a HPLC purity of ≥95%, as determined using a C18 chromatographic column, using as the mobile phase (1) water and acetonitrile at 95:5 for 25 minutes, then (2) water and acetonitrile at 10:90 for 6 minutes, then (3) water and acetonitrile at 95:5 for 5 minutes, wherein the compound of formula (I) is

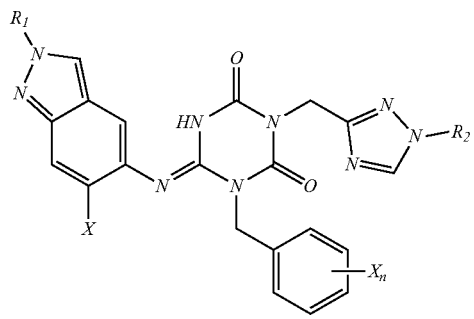

formula (I)

wherein $R_1$ and $R_2$ are each independently $C_1$-$C_6$ alkyl;

X is halogen;

n is an integer from 1 to 5, and a compound (6E)-6-[(6-chloro-1-methyl-1H-indazol-5-yl)imino]-3-[(1-methyl-1H-1,2,4-triazol-3-yl) methyl]-1-(2,4,5-trifluorobenzyl)-1,3,5-triazinane-2,4-dione, as an impurity in the composition, has a content of <0.1%.

43. The composition according to claim 42, in which the composition does not comprise the compound (6E)-6-[(6-chloro-1-methyl-1H-indazol-5-yl)imino]-3-[(1-methyl-1H-1,2,4-triazol-3-yl) methyl]-1-(2,4,5-trifluorobenzyl)-1,3,5-triazinane-2,4-dione.

44. The composition according to claim 42, in which the compound of formula (I) is 45. The composition according to claim 42, in which the composition is obtained from a method for purifying, and the method for purifying comprises the following steps:

(ii) dispersing the compound of formula (I) to be purified in one or more solvents, optionally heating, stirring and/or cooling, followed by filtrating to obtain the composition comprising the compound of formula (I).

46. The composition according to claim 45, in which the method for purifying comprises the following steps:

(i-a) recrystallizing a to-be-purified composition comprising the compound of formula (I) in a mixed solvent; and (ii-a) dispersing solid obtained in the step (i-a) in one or more solvents, optionally heating, stirring and/or cooling, followed by filtrating to obtain the composition comprising the compound of formula (I);

or (ii-b) dispersing the compound of formula (I) to be purified in one or more solvents, optionally heating, stirring and/or cooling, followed by filtrating to obtain a solid; and (i-b) recrystallizing the solid obtained in the step (ii-b) in a mixed solvent.

47. The composition according to claim 45, in which in the step (ii), the heating is performed at a temperature in the range of 40-80° C.;

in the step (ii), the cooling is performed at a temperature in the range of 0-35° C.;

and/or, in the step (ii), the solvent is water, $C_1$-$C_6$ alkyl alcohol, di-$C_1$-$C_6$ alkyl ether and/or $C_1$-$C_6$ alkyl ketone.

48. The composition according to claim 46, in which the step (i-a) or (i-b) further comprises filtering the solid obtained from recrystallization; and/or, the step (i-a) or (i-b) and/or the step (ii-a) or (ii-b) further comprises drying the solid.

49. The composition according to claim 46, in which in the step (i-a) or (i-b), the mixed solvent is a mixture of any two of $C_1$-$C_6$ halogenated alkane, $C_1$-$C_6$ alkyl carboxylic acid and di-$C_1$-$C_6$ alkyl ether.

50. The composition according to claim 45, in which the composition is a white solid.

51. The composition according to claim 42, in which the composition is obtained from a method for preparing, and the method for preparing comprises the following steps:

(a) reacting a compound of formula (II)

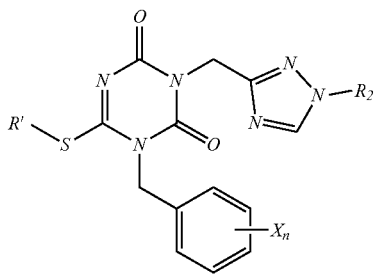

formula (II)

wherein,
R' is $C_1$-$C_6$ alkyl;
$R_2$, X and n are as defined in formula (I);
with a compound of formula (III)

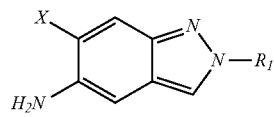

formula III wherein,
$R_1$ and X are as defined in formula (I);
in the presence of a base added in portions and/or a co-solvent to obtain the composition comprising the compound of the formula (I).

52. The composition according to claim 51 in which the compound of formula (II) is synthesized by the following steps:
(b) reacting a compound of formula (IV)

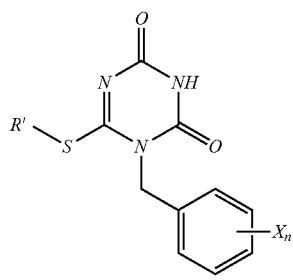

formula IV wherein,
R', X and n are as defined in formula (II); with a compound of formula (V) or a salt thereof

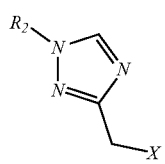

formula (V)

wherein,
$R_2$ and X are as defined in formula (II);
to obtain the compound of formula (II).

53. The composition according to claim 51, in which the co-solvent is selected from the group consisting of dioxane, $C_1$-$C_6$ alkyl ketone, $C_1$-$C_6$ alkyl alcohol, dimethylacetamide, dimethylformamide, acetonitrile, dimethylsulfoxide, N-methylpyrrolidone, and any mixture thereof.

54. The composition according to claim 51, in which the base added in portions is the base added in two or more portions.

55. The composition according to claim 51, in which the method for preparing further comprises a purification step.

56. The composition according to claim 55, in which the purification step is a column chromatography and/or recrystallization step.

57. The composition according to claim 51, in which X is fluorine or chlorine; and/or, n is an integer from 2 to 4.

58. A composition, comprising a physiologically acceptable salt of a compound of formula (I), in which the physiologically acceptable salt of the compound of formula (I) has a HPLC purity of ≥99%, as determined using a C18 chromatographic column as determined using a C18 chromatographic column, using as the mobile phase (1) water and acetonitrile at 95:5 for 25 minutes, then (2) water and acetonitrile at 10:90 for 6 minutes, then (3) water and acetonitrile at 95:5 for 5 minutes, wherein the compound of Formula (I) is.:

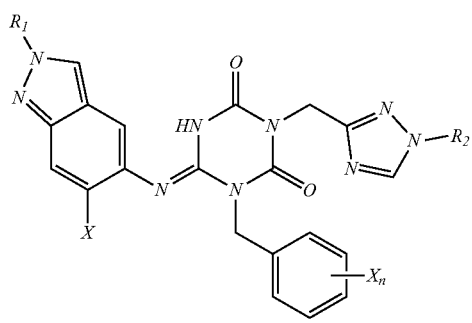

formula (I)

wherein
$R_1$ and $R_2$ are each independently $C_1$-$C_6$ alkyl;
X is halogen;
n is an integer from 1 to 5, and
a compound (6E)-6-[(6-chloro-1-methyl-1H-indazol-5-yl) imino]-3-[(1-methyl-1H-1,2,4-triazol-3-yl) methyl]-1-1-(2,4,5-trifluorobenzyl)-1,3,5-triazinane-2,4-dione, as an impurity in the composition, has a content of <0.1%, wherein the physiologically acceptable salt of the compound of formula (I) is a fumarate salt.

59. The composition according to claim 58, wherein the composition does not comprise the compound (6E)-6-[(6-chloro-1-methyl-1H-indazol-5-yl)imino]-3-[(1-methyl-1H-1,2,4-triazol-3-yl) methyl]-1-(2,4,5-trifluorobenzyl)-1,3,5-triazinane-2,4-dione.

60. The composition according to claim 58, wherein the compound of formula (I) is

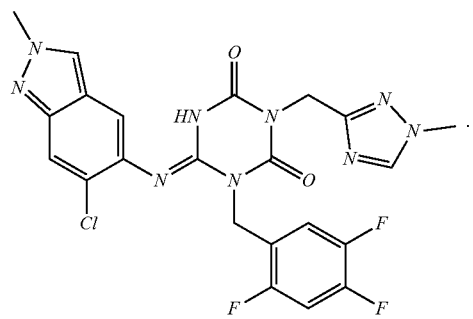
\* \* \* \* \*